(12) United States Patent
Potter

(10) Patent No.: US 12,307,471 B2
(45) Date of Patent: May 20, 2025

(54) METHODS AND SYSTEMS FOR GROWING AND RETAINING THE VALUE OF BRAND DRUGS BY COMPUTER PREDICTIVE MODEL

(71) Applicant: Myrtle S. Potter, Dunwoody, GA (US)

(72) Inventor: Myrtle S. Potter, Dunwoody, GA (US)

( * ) Notice: Subject to any disclaimer, the term of this patent is extended or adjusted under 35 U.S.C. 154(b) by 0 days.

(21) Appl. No.: 18/759,871

(22) Filed: Jun. 29, 2024

(65) Prior Publication Data

US 2024/0354783 A1    Oct. 24, 2024

Related U.S. Application Data

(63) Continuation of application No. 18/111,890, filed on Feb. 21, 2023, now Pat. No. 12,026,732, which is a continuation of application No. 17/352,220, filed on Jun. 18, 2021, now Pat. No. 11,593,820, which is a continuation of application No. 16/563,471, filed on Sep. 6, 2019, now Pat. No. 11,042,889, and a continuation of application No. 15/900,456, filed on Feb. 20, 2018, now Pat. No. 10,410,307, which is a continuation of application No. 14/214,636, filed on Mar. 14, 2014, now abandoned.

(60) Provisional application No. 61/801,978, filed on Mar. 15, 2013.

(51) Int. Cl.
G06Q 30/0201      (2023.01)
G06Q 30/0241      (2023.01)
G16H 20/10        (2018.01)
G16H 70/40        (2018.01)

(52) U.S. Cl.
CPC ..... *G06Q 30/0201* (2013.01); *G06Q 30/0276* (2013.01); *G16H 20/10* (2018.01); *G16H 70/40* (2018.01)

(58) Field of Classification Search
CPC .......... G06Q 30/0201; G06Q 30/0276; G16H 70/40; G16H 20/10
USPC .............................................................. 705/2
See application file for complete search history.

(56) References Cited

U.S. PATENT DOCUMENTS

| | | | |
|---|---|---|---|
| 5,692,107 A * | 11/1997 | Simoudis ............... | G06N 5/025 706/45 |
| 6,430,539 B1 * | 8/2002 | Lazarus ................. | G06Q 30/02 705/14.1 |
| 8,155,993 B2 * | 4/2012 | de Nijs ............. | G06Q 30/0201 705/7.29 |
| 11,593,820 B2 * | 2/2023 | Potter .................... | G16H 70/40 |

(Continued)

*Primary Examiner* — Michael Tomaszewski
(74) *Attorney, Agent, or Firm* — RADLO & SU

(57) ABSTRACT

The present invention is directed to a brand value growth and retention system for brand drugs commercialized by brand drug advertisers through a brand drug's lifecycle during patent exclusivity and after loss of exclusivity. The brand value growth and retention system iteratively analyzes combined computational models of consumer, healthcare provider retailer and payor segment data to produce brand drug promotional campaigns that are predictive with modifying parameters that transform the promotional campaigns over time. As a result, the brand drug promotional campaign generates an increased number of brand drug purchases while predicting the point where incremental promotional campaign investments produce a diminishing number of incremental brand drug purchases.

14 Claims, 18 Drawing Sheets

(56) References Cited

U.S. PATENT DOCUMENTS

| | | | | |
|---|---|---|---|---|
| 2002/0052775 A1* | 5/2002 | Fisher, Jr. | ............... | G06Q 30/02 |
| | | | | 705/7.29 |
| 2005/0278185 A1* | 12/2005 | de Nijs | .............. | G06Q 10/0639 |
| | | | | 705/400 |
| 2010/0287029 A1* | 11/2010 | Dodge | .................. | G06Q 30/02 |
| | | | | 705/7.31 |
| 2011/0173018 A1* | 7/2011 | Hoffner | ................. | G06Q 30/02 |
| | | | | 706/50 |
| 2013/0006662 A1* | 1/2013 | Soto | ....................... | G06Q 10/04 |
| | | | | 705/2 |
| 2013/0006711 A1* | 1/2013 | Biswas | ................. | G06Q 30/02 |
| | | | | 705/7.33 |
| 2013/0282436 A1* | 10/2013 | Quinn | ................. | G06Q 30/0202 |
| | | | | 715/846 |
| 2014/0278507 A1* | 9/2014 | Potter | .................... | G16H 20/10 |
| | | | | 705/2 |
| 2015/0262257 A1* | 9/2015 | Suess | ................ | G06Q 30/0276 |
| | | | | 705/14.72 |
| 2021/0312480 A1* | 10/2021 | Potter | ................ | G06Q 30/0201 |
| 2022/0336111 A1* | 10/2022 | Ohana | ...................... | G06N 3/09 |
| 2023/0206257 A1* | 6/2023 | Potter | .................... | G16H 20/10 |
| | | | | 705/2 |

* cited by examiner

| promotional tactics/segments | 1 | 2 | 3 | 4 | 5 | 6 | 7 | ... | m | |
|---|---|---|---|---|---|---|---|---|---|---|
| 1 | | — | | — | | | — | | | SPP1 |
| 2 | | — | — | — | | | — | | | SPP2 |
| 3 | | | | | | | | | | SPP3 |
| 4 | — | — | — | — | | — | | | — | SPP4 |
| 5 | | — | — | — | | — | | | — | SPP5 |
| 6 | — | — | — | — | — | — | | | — | SPP6 |
| 7 | | — | — | | | — | | | — | SPP7 |
| ... | | — | | — | | — | | | — | SPP8 |
| n | | | | — | | — | | | — | SPPn |

Columns labeled: 61 (promotional tactics/segments), 60, 63a (tactic profile), 65 Promotional Campaign (PC), 63b (tactic profile), 63c (tactic profile), 64 (SPP1), 66 (SPP2), 67 (SPP3), 68 (SPPn), 62, 59

74 Brand Drug Volume (y-axis)
73 Promotional Pressure (x-axis)

- 69 / 75 — promotional tactic 1
- 70 / 76 — promotional tactic 2
- 71 / 77 — promotional tactic 3
- 72 / 78 — promotional tactic 4

METHODS AND SYSTEMS FOR GROWING AND RETAINING THE VALUE OF BRAND DRUGS BY COMPUTER PREDICTIVE MODEL

CROSS REFERENCE TO RELATED APPLICATIONS

This application is a continuation of U.S. Nonprovisional application Ser. No. 18/111,890, filed on 21 Feb. 2023, now U.S. Pat. No. 12,026,732, which is a continuation of U.S. Nonprovisional application Ser. No. 17/352,220, filed on 18 Jun. 2021, now U.S. Pat. No. 11,593,820, which is a continuation of U.S. Nonprovisional application Ser. No. 16/563,471, filed on 6 Sep. 2019, now U.S. Pat. No. 11,042,889, which is a continuation of U.S. Continuation application Ser. No. 15/900,456, filed on 20 Feb. 2018, now U.S. Pat. No. 10,410,307, which is a continuation of U.S. Nonprovisional application Ser. No. 14/214,636, filed on 14 Mar. 2014, which claims priority to U.S. Provisional Application Ser. No. 61/801,978 entitled "Methods and Systems for Growing and Retaining the Value of Brand Drugs by Computer Predictive Modeling," filed on 15 Mar. 2013, the disclosures of which are incorporated herein by reference in their entireties.

BACKGROUND

Technical Field

The present invention relates generally to process and optimization software, and more particularly to computer predictive models of consumer, healthcare provider, retailer, pharmacy and payor segment data to generate a flexible, responsive and adaptive promotional campaign for growing and retaining the value of brand drugs during a drug's lifecycle including its launch phase, growth phase as well as the phase around the time of loss of exclusivity (LOE).

Related Art

Brand drugs marketed by most brand drug advertisers provide the basis upon which many of these companies are able to meet consumer medical needs and generate revenue and profits during a brand drug's lifecycle. The brand drug lifecycle also overlaps with the period of market exclusivity defined by the brand drug's patents. This period of market exclusivity provides years of market sales monopoly for the brand, but, at the same time, it imposes a limited duration of revenue and profit due to the expiration of the associated patents. As brand drug patents expire, brand drug advertisers confront the inevitable risk of rapid and significant loss of revenue and profits.

Each year, billions of dollars of brand drugs lose exclusivity thereby opening the way for generic manufacturers to enter the market with the same or similar drug at greatly discounted prices. It is estimated that in the United States $267 billion of brand drugs will lose patent exclusivity from 2010 to the end of 2016, and more than $50 of billion brands will become generic within the following five years. A brand drug's sales during its lifecycle often reach peak at the time of LOE; such was the case for Singulair. The annual sales of Singulair at the time of loss of exclusivity were approximately $3.3 billion, making it the biggest selling prescription drug for its manufacturer, Merck. After losing its patent exclusivity Singulair suffered a precipitous and material decline in revenue and profit with sales dropping 90% in just four weeks. It is estimated that brand drugs typically retain significantly less than 10% brand share when reaching the period of post-exclusivity.

Brand drug advertisers have long been known to invest billions of dollars to bolster the sales of their brand drugs. Second to drug research and development costs, the combined costs of sales, marketing and promotion far exceed any other single expense item for most Brand drug advertisers. A major and recurring challenge for brand drug advertisers is the lack of predictive methods that can be applied to the combined individual promotional investment decisions for brand drugs to drive the highest sales of brand drugs while at the same time predicting the point at which massive investments in promotion no longer produce incremental value. There is a need for a real-time, predictive system that combines the correlations of various consumer, healthcare provider, retailer and payor segment data for predictive value. The benefits of such a system for brand drug advertisers are greater brand sales at significantly lower costs. With the growing pressure to contain healthcare system costs, methods such as the brand drug value growth and retention system as described below can have a meaningful and material impact on the industry.

Given the finite time that brand drug advertisers' patents allow for the exclusive sale of the related brands, it is desirable to grow and retain brand drug value during the brand's lifecycle, which includes its launch phase, growth phase and the phase around the loss of exclusivity phase. It is therefore desirable to have a software predictive model to generate, apply, refine, modify, transform, and improve, with a feedback mechanism through machine learning, one or more promotional campaigns for growing and retaining brand drug value.

SUMMARY

Methods, computer program products, and computer systems are described for growing and retaining the value of brand drugs by predictive computational modeling of consumer segment, healthcare provider segment, retailer segment, and payor segment data to generate a promotional campaign during a brand drug launch phase, growth phase, or around the loss of exclusivity phase. A brand drug value growth and retention engine comprises a financial model simulator module, a consumer segments module, a healthcare segments module, a retailer segments module, a promotional campaign module, a manufacturer copay card pricing module, a manufacturer brand execution module, and other modules. The consumer segments module is configured to provide a computational modeling of consumer segments to determine an optimal promotional plan for a directed consumer segment for a brand drug. The healthcare provider module is configured to provide a computational modeling on healthcare provider segments for the brand drug. The manufacturer PBM/payor strategy module and the manufacturer PBM/payor execution module are configured to provide a computational model of payor segments. The financial model simulator module is configured to receive the computational model consumer segment data, the computational model healthcare provider segment data, and the computational model payor segment data, and executes a predictive model of promotional tactics to segments of the consumers, healthcare providers and payors to produce an optimal promotional campaign for the specified brand drug.

A promotional campaign represents a combination of segment promotional plans. A first set of segment promotional plans is for rolling out to consumer segments, where each segment promotional plan has one or more tactic profiles. A tactic profile is applicable when a particular consumer segment responds well to the directed promotional tactic. A second set of segment promotional plans rolls out to healthcare provider segments, where each segment promotional plan has one or more tactic profiles. A tactic profile is applicable when a particular healthcare provider segment, which can be grouped by behavior of individual healthcare providers, responds well to the directed promotional tactic. A third set of segment promotional plans rolls out to payor segments, where each segment promotional plan has one or more tactic profiles. A tactic profile is applicable when a particular healthcare provider segment, which can be grouped by behavior of individual healthcare providers, responds well to the directed promotional tactic.

The brand drug value growth and retention engine includes a dashboard interface module configured to provide a user interface to communicate data and control information between the brand drug value growth and retention engine and a master dashboard located at the computer device of the brand strategist. The dashboard is partitioned into different sections for displaying the consumer segment data, healthcare provider data and payor segment data, as well as the predictive modeling result of a recommended promotional campaign. Alternative segment promotional plans are also provided when the current promotional campaign is less than optimal as determined by the financial model simulator module.

Broadly stated, a method for selecting a promotional campaign in the healthcare industry, comprising executing a first computational model on the consumer segments data to determine a first substantially optimal brand drug promotional mix for consumers who are candidates for a brand-name drug; executing a second computational model on healthcare provider segments data to determine a second substantially optimal brand drug promotional mix for healthcare providers who treat the consumers who are candidates for the brand-name drug; executing a third computational model on payor segment data to determine a substantially optimal contracting strategy for the brand-name drug; and generating a promotional campaign for the brand-name drug by running a predictive model of the consumer segments data, healthcare provider segments data and payor segment data, based on the combination of outputs from the first, second and third computational models.

Advantageously, the present invention is an effective predictive model for generating and optimizing a promotional campaign for brand drug advertisers to grow and retain the value of brand drugs when launching or growing a product, or around the time of patent expiration.

The structures and methods of the present invention are disclosed in the detailed description below. This summary does not purport to define the invention. The invention is defined by the claims. These and other embodiments, features, aspects, and advantages of the invention will become better understood with regard to the following description, appended claims and accompanying drawings.

BRIEF DESCRIPTION OF THE DRAWINGS

The invention will be described with respect to one or more various embodiments thereof, and reference will be made to the drawings. The drawings are provided for purposes of illustration and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

DETAILED DESCRIPTION

Figure 1:
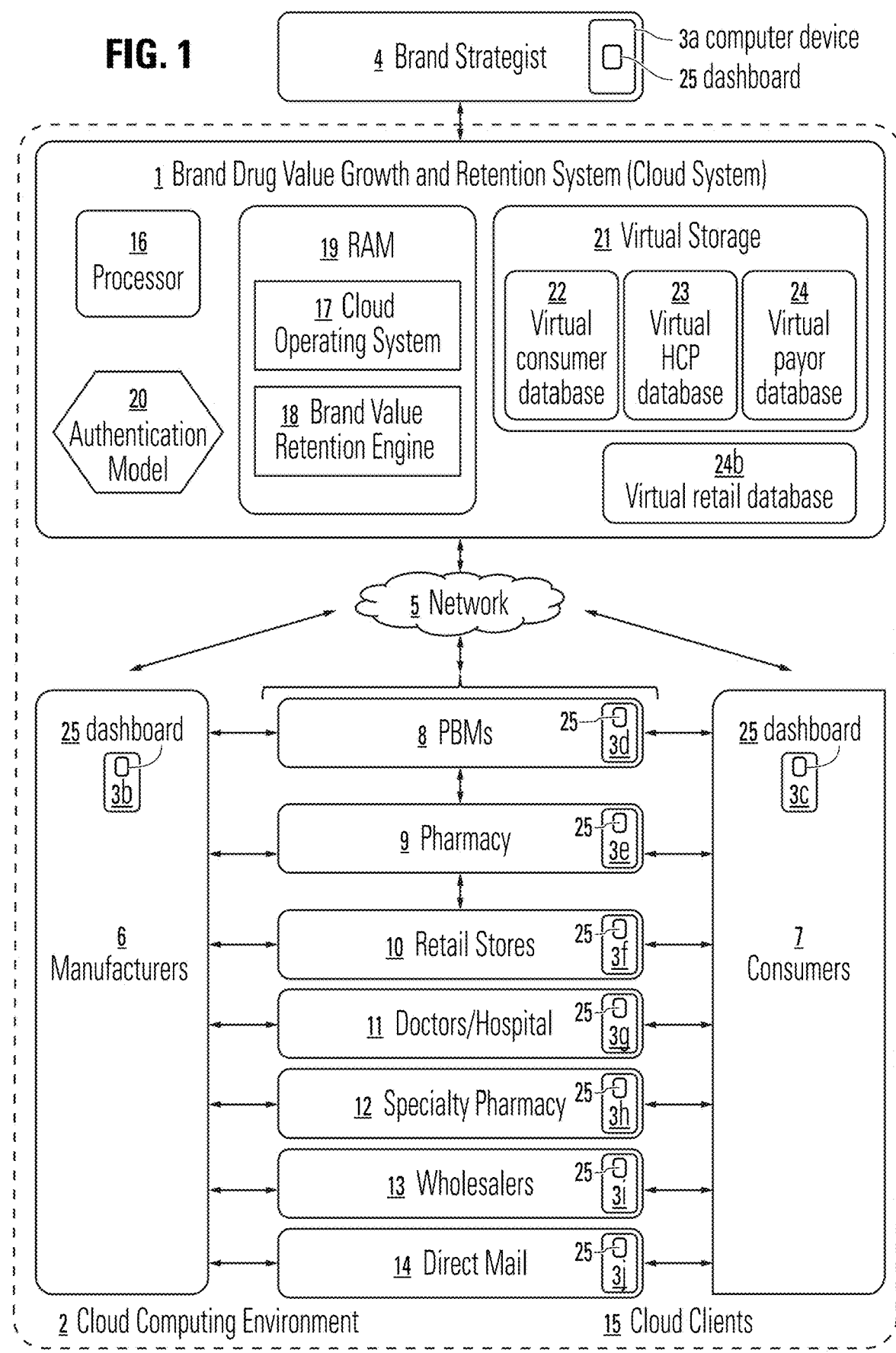
FIG. 1 is a high-level block diagram illustrating a brand drug value growth and retention system in a cloud computing environment in accordance with the present invention.

A description of structural embodiments and methods of the present invention is provided with reference to FIGS. 1-10. It is to be understood that there is no intention to limit the invention to the specifically disclosed embodiments but that the invention may be practiced using other features, elements, methods, and embodiments. Like elements in various embodiments are commonly referred to with like reference numerals.

The following definitions may apply to some of the elements described with regard to some embodiments of the invention. These terms may likewise be expanded upon herein.

Brand Drug—refers to a medication, including prescription drugs, over the counter (OTC) drugs, and supplements that are associated with a proprietary trade name, often have a trade mark, and that in many cases have patents that provide monopolistic market protections for a finite amount of time and/or intellectual property protections.

Brand Drug Advertisers—refers to manufacturers and retailers.

Brand Samples—refers to small quantities of free brand drugs provided by a brand drug advertiser for distribution by healthcare providers to consumers or directly to consumers.

Brand Strategist-refers to a person who monitors or directs the monitoring of market and brand drug trends and oversees the planning, management and execution of brand drug analyses, planning, pricing, contracting, advertising and promotional campaigns and insures that tactics are being delivered to consumers, healthcare providers and payors to achieve desired outcomes. The brand strategists may or may not be an employee of the manufacturer.

Computational Model (also referred to as "computational modeling," "computer model," or "computer modeling"—refers to any software that models an external process (such as a promotional campaign).

Consumer Segmentation—refers to the process of defining and subdividing a large homogenous group of consumers who are currently using or who are candidates for using brand drugs into clearly identifiable groups having similar demographics, needs, wants, demand characteristics or behaviors for the purpose of designing a segment promotional plan that matches the expectations of consumers in the segments. In one embodiment, which is not intended to limit the various constructions of a consumer segmentation, within this identified population the entire pool of consumers is subdivided based on sub-regions or segments that make up the whole geography. For example, in California, a state may be divided into 25 segments, such as San Francisco, Oakland, San Diego, Los Angeles, Santa Barbara, etc.

Copay Card—refers a multiple use or single use tool through which rebates and purchase discounts are offered to a consumer who uses, or is a candidate for, a particular brand drug. Copay cards come in many forms including plastic, paper or any electronic equivalent on a computer, smartphone, tablet or wearable device. Copay cards are most often financed by brand drug advertisers.

Coupon—refers to a voucher entitling the holder to rebates and purchase. Coupons come in many forms including plastic, paper or any electronic equivalent on a computer, smartphone, tablet or wearable device. Coupons are most often financed by brand drug advertisers Direct to Consumer (DTC)—refers to a form of brand drug advertising that is directed toward consumers, rather than healthcare professionals.

Distribution Channels—refers to networks of organizations, including manufacturers, brand drug advertisers, wholesalers, retailers and pharmacies supply brand drugs to consumers.

Elasticity Curve—refers to a measure used to show the responsiveness, or elasticity, of the ratio of the percentage change in at least one variable to the percentage change in another variable.

Finite Post-LOE Phase—refers to a predetermined period of time as set forth by U.S. Patent Law that allows for certain brand drugs to exist on the market with a restricted number of generic competitors.

Formulary—refers to a list or database of brand drugs. The main function of a formulary is to specify the drugs that are approved to be prescribed by healthcare providers under a particular contract with a payor who provides a drug benefit plan to consumers. Consumers pay varying portions of the cost of the drug (known as a copay) for prescription drugs that are on formulary based on which drugs are preferred by the payor. For drugs that are not on formulary, consumers must pay a larger percentage of the cost of the drug, sometimes 100%. Formularies vary between drug plans and differ in the breadth of drugs covered and costs of copay and the drug insurance benefit premium. Most formularies encourage generic substitution.

Healthcare Provider—refers to physicians, doctors, nurses, physician assistants, dentists, optometrists, podiatrists, osteopaths, or any individual who has the state or federal government authority to prescribe drugs as well as those whose industry stature and influence constitute them as being brand drug thought leaders.

Healthcare Provider Segmentation—refers to the process of defining and subdividing a large homogeneous group of healthcare providers. One embodiment of the physician segmentation is to divide the entire population of physicians into clearly identifiable groups having similar demographics, needs, wants, demand characteristics or behaviors for the purpose of designing a segment promotional plan that matches the expectations of physicians in the segments. For example, within a given population of physicians, physicians who are surgeons may be segmented as one group, and family doctors may be part of a different group or segmentation.

Key parameter—refers to a parameter, typically numerically-valued in a predictive element or model or learning machine whose value affects the quality of the prediction. For instance, a key parameter can be associated with each factor of a drug—cost, availability, generic competition (if any), and side effects—that a predictive model would use in order to generate a promotional tactic or segment promotional plan or promotional campaign. Key parameters may be set manually from experience or may be estimated by a learning machine.

Learning Machine—refers to a software system that creates a predictive model or more typically infers, refines and adapts the parameters of a predictive model based on past or current training data. Examples of learning machines include decision trees, random forests, Bayesian classifiers, neural networks, support vector machines, and logistic regression.

Loss of exclusivity (LOE)—refers to the expiration of patents granted by the U.S. Patent and Trademark Office, which is calculated by standard duration of a patent plus any applicable Patent Term Adjustment (PTA).

Loyalty Cards (also known as Affinity Cards)—a plastic or paper card, visually similar to a credit card or debit card, or digital card that identifies the cardholder as a member in a loyalty or affinity program. By presenting the card, the purchaser is typically entitled to either a discount on purchases, or points, credits, rewards, rebates or credits that can be used for current or future purchases or for merchandise rewards.

Manufacturers—refers to companies that research, develop, produce, and/or market drugs licensed for use as medications including but not limited to pharmaceutical companies, biotech companies and consumer packaged goods companies.

Optimal—inclusive of both the mathematical meaning of the best or highest-valued outcome, and a looser general meaning of producing an outcome better than others considered given a limited level of computation or effort. It is often the case that optimality can be approximated closer with increasing effort or computation (such as in submodular functions, http://en.wikipedia.org/wiki/Submodular_set_function), but for practical reasons, such as diminishing returns, the computation is halted with the best results so far, and that result is labeled "optimal," or "optimal" for the effort expended. This is also called "near optimal" or "approximately optimal" in the art.

Payor—refers to entities other than the consumer that finance or reimburse the cost of brand drugs. This term refers to PBMS, health insurance companies, other third-party payors or health plan sponsors (e.g. employers or unions).

Pharmacy Benefit Manager (PBM)—refers to third-party administrators of prescription drug insurance benefit programs who are primarily responsible for processing and paying prescription drug insurance claims and supplying prescription drugs via mail distribution channels to consumers. PBMs also develop and maintain drug formularies http://en.wikipedia.org/wiki/Formulary, enter contract arrangements with pharmacies, and negotiate discounts and rebates with drug manufacturers. Currently a majority of Americans receive prescription drug benefits administered by PBMs.

Predictive—refers to generating an expectation of a future outcome based on presently available information.

Predictive Element—refers to a computer model or program that, given a set of inputs, uses one or more methods internally to predict a tactic and/or outcome optionally with a weight or confidence score. For instance, given attributes of a certain consumer segment, such as cost-sensitivity, medial needs etc., a predictive element would generate a tactic (e.g. a way to reach best reach this targeted consumer segment) and optionally a measure of estimated effectiveness.

Predictive Model—refers to an automated or semi-automated process of generating a prediction based on a model, typically combining software and data. The model may be programmed in software and its parameters (e.g. weights) modified or optimized by a learning machine or by a domain expert.

Promotional Campaign—refers to a combination of segment promotional plans which consumer, healthcare provider, retailer, pharmacy or payor segments are responsive to specific promotional tactic profiles deployed during a brand drug product launch phase, growth phase, or around the brand drug's loss of exclusivity phase.

Promotional Channels—refers to the physical distribution network or electronic distribution networks (meaning computer communication media or handheld devices) through which brand drug promotional campaigns are distributed to patients, consumers, healthcare providers and/or payors.

Promotional Mix—refers to specific combination of promotional methods d for a brand drug. Elements of a promotion mix may include print advertising, DTC advertising, digital advertising or other means of advertising.

Promotional Tactics—refers to a collection of tactics deployed to a particular segment of consumers, healthcare providers or payors pertaining to a brand drug. Some popular promotional tactics include TV advertisement, Internet advertisement, social networking advertisement, direct mail advertisement, presentations by sales representatives either by telephone, computer, mobile device or in person, and copay cards.

Retail (retail stores, retailer)—refers to pharmacies, supermarkets, grocery stores, big box stores and other retail outlets.

Sales Presentation—refers to detailed information about a product or product-line that is presented by a sales person or sales team face to face or electronically to a healthcare provider, PBM or payor for the purpose of convincing the healthcare provider, PBM or payor to use or allow the use of a brand drug or set of brand drugs.

Segment Promotional Plans—refers to each segment promotional plan comprised of a collection of tactic profiles that have been determined to be effective and responsive with a particular consumer segment, healthcare provider segment, retailer or payor segment.

Switch Data—refers to consumer and payor prescription transaction data created by certain systems technology companies for the purpose of managing and monitoring the processing of prescription drug claims and claims payment cycles. These data are often provided to or sold to healthcare providers, pharmacies, wholesalers, retailers, PBMs, payers or others.

Tactic Profile refers to a promotional tactic to which a particular consumer segment, healthcare provider segment, retailer segment or payor segment responds, either positively, negatively or neutrally.

Quadripartite Model—refers to a computer-implemented combination of four different models or predictive elements that generates a joint or combined prediction. For instance, a combination of a healthcare provider element, a payor (e.g. insurance) element, and a consumer or consumer group element.

System Architecture

FIG. 1 is a high-level block diagram illustrating one embodiment of a brand drug value growth and retention system 1 in a cloud computing environment 2 for conducting a predictive model for growing and retaining the value of brand drugs. The brand drug value growth and retention system 1 is coupled to a computer device 3a of a brand strategist 4 and through a network 5 to a computer device 3 of brand drug manufacturers 6, a computer device 3 of consumers 7, and other intermediaries between the drug manufacturers 6 and the consumers 7. Each of the intermediaries, PBMs 8, pharmacies 9, retailers stores 10, doctors and hospitals 11, special pharmacies 12, wholesalers 13, and direct mail prescription providers 14 has an associated respective computer device 3d, 3e, 3f, 3g, 3h, 3i and 3j. Collectively, the brand drug manufacturers 6, the consumers 7, and the intermediaries operate as cloud clients 15. The cloud clients 15 communicate with the brand value growth and retention system 1 through the network 5, either wirelessly or via a wired connection. The retail stores 10 include supermarkets, groceries, pharmacies and other retail segments.

The brand value growth and retention system 1 includes a computer processor 16 for executing a cloud operating system 17 and a brand drug value growth and retention engine 18, which are configured on a random access memory (RAM) 19. An authentication module 20 is also part of the brand drug value growth and retention system 1 for authenticating a cloud client. The brand drug value growth and retention system 1 also includes a virtual storage 21, which includes a virtual consumer database 22 for storing consumer data, a virtual healthcare provider (HCP) database 23 for storing healthcare provider data, a virtual payor database 24 for storing PBM/payor segment data, and a virtual retail database 24b for storing retail data. The computer device 3a has a master dashboard 25, which displays data for viewing and assessing by the brand strategist 4. The brand drug manufacturers 6, the consumer 7, and the intermediaries also have a dashboard 25 at their disposal located in their respective computer devices.

The cloud system 2 is also referred to as web/Hypertext Transfer Protocol (HTTP) server. Alternatively, the authentication module 20 can be a separate server, which may employ a variety of authentication protocols to authenticate the user, such as a Transport Layer Security (TLS) or Secure Socket Layer (SSL), which are cryptographic protocols that provide security for communications over networks like the Internet. The protocols described herein are merely exemplary, and embodiments of the present invention include other emerging and new protocols.

In one embodiment, the cloud computer system 2 is a browser-based operating system communicating through an Internet-based computing network that involves the provision of dynamically scalable, and often virtualized, resources as a service over the Internet, such as iCloud® available from Apple Inc. of Cupertino, Calif., Amazon Web Services (IaaS) and Elastic Compute Cloud (EC2) available from Amazon.com, Inc. of Seattle, Wash., SaaS and PaaS available from Google Inc. of Mountain View, Calif., Microsoft Azure Service Platform (Paas) available from Microsoft Corporation of Redmond, Wash., Sun Open Cloud Platform available from Oracle Corporation of Redwood City, Calif., and other cloud computing service providers.

The web browser is a software application for retrieving, preenting and traversing a Uniform Resource Identifier (URI) on the World Wide Web provided by the cloud computer 2 or web servers. One common type of URI begins with HTTP and identifies a resource to be retrieved over the HTTP. A web browser may include, but is not limited to, browsers running on personal computer operating systems and browsers running on mobile phone platforms. The first type of web browsers may include Microsoft's Internet Explorer, Apple's Safari, Google's Chrome, and Mozilla's Firefox. The second type of web browsers may include the iPhone OS, Google Android, Nokia S60 and Palm WebOS. Examples of a URI include a web page, an image, a video, or other type of content.

The network 5 can be implemented as a wireless network, a wired network protocol or any suitable communication protocol, such as 3G (third-generation mobile telecommunications), 4G (fourth-generation cellular wireless standards), long-term evolution (LTE), 5G, a wide area network (WAN), Wi-Fi™ like wireless local area network (WLAN) 802.11n, or a local area network (LAN) connection (internetwork—connected to either WAN or LAN), Ethernet, Bluebooth™, high frequency systems (e.g., 900 MHz, 2.4 GHz and 5.6 GHz communication systems), infrared, transmission control protocol/internet protocol (TCP/IP) (e.g., any of the protocols used in each of the TCP/IP layers), hypertext transfer protocol (HTTP), BitTorrent™, file transfer protocol (FTP), real-time transport protocol (RTP), real-time streaming protocol (RTSP), secure shell protocol (SSH), any other communications protocol and other types of networks like a satellite, a cable network, or optical network set-top boxes (STBs).

The brand drug manufacturers 6 have various distribution channels to distribute brand drugs to the consumers 7. FIG. 1 shows one embodiment of such distribution channels, but the present invention is not limited to this embodiment. Various distribution channels are also applicable. In one embodiment, after the pharmacy benefit manager (PBM) 8 receives brand drugs from manufacturers 6, the PBM 8 distributes brand drugs to the pharmacy 9, which then sells the drugs to the consumers 7. The PBM 8 may also deliver the drugs via the mail to consumers on behalf of health plan providers.

A consumer obtains their brand drugs from a variety of sources, of which six exemplary sources are provided herein. The first source from which consumers can get their brand drugs is from a hospital 11 or prescribed by a doctor directly because the doctor office sometimes operates as a point of sale location. The second source of distribution channel is a pharmacy 9, such as CVS, Walgreens, independent pharmacies etc., where the consumer can purchase brand drugs. A third source from which the consumer may obtain brand drugs is from a PBM 8. A fourth channel of distribution is a wholesaler 13, which buys large quantities of brand drugs to resell to retail stores, PBMs, physician offices, hospitals, consumers and others. A special pharmacy 12 provides a fifth source for drug distribution. A sixth source of is retail stores 10 such as grocery stores, big box stores etc. Overall, manufacturers 6 have numerous channels to distribute brand drugs to consumers and to ensure that consumers use the drugs as prescribed.

The distribution channels of drugs are becoming more integrated, offering brand drug advertisers, manufacturers 6 and consumers 7 more active and direct interactions. The majority of the consumers who have an insurance drug benefit get their drugs through a PBM. The PBM 8 operates on behalf of payors and distributes the prescription drugs to pharmacies 9, retail stores 10, hospitals 11 or directly to consumers 7. As a distribution channel, the PBMs 8 are an integrated delivery network in which synchronized consumer information flows across different entities enabling a more direct communication between manufacturers 6 and consumers 7. Additionally, PBM companies have the capability to distribute prescription infusible drugs because PBM companies may also have special distribution channels, such as specialty pharmacies 12 that carry infusible drugs and other specialty pharmaceutical products for certain patients such as those with cancer, hemophilia, cystic fibrosis, organ transplant, etc. The PBMs 8 are highly automated and are able to offer efficient service to consumers, including mailing order prescriptions. Specialty pharmacies 12 also exist as independent entities distinct and separate from PBMs.

In addition to being key components in the distribution infrastructure, drug manufacturers 6 are often able to control the pricing of the brand drugs sold to consumers 7 during the exclusivity period. The brand value growth and retention system is used as a software tool to maintain a prescription drug's pricing for the drug manufacturers 6 during the period preceding and after the loss of exclusivity date. The brand drug value growth and retention engine also produces a promotional campaign after the exclusivity period ends to retain the value of a branded drug for the brand drug advertisers and manufacturers 6. During the distribution process from the manufacturers 6 to the consumers 7, a brand drug value growth and retention system can be put in place, which increases the likelihood that a consumer will stay with a specific brand drug for a period of time, even after the brand drug has lost its exclusivity. Essentially, the brand drug value growth and retention engine creates a new period of commercialization, and its software facilitates the retention of brand value for brand drugs after the exclusivity period has ended. Additionally, the brand drug value growth and retention engine software allows the storage of a massive amount of consumer information in the virtual storage 21. The virtual consumer database that can also be linked to healthcare provider, retailer and payor virtual databases 22, 23, 24, 25. In some embodiments, a consumer would make a choice to opt-in to the consumer virtual database. In turn, in one embodiment the consumer virtual database and the HCP virtual database are systems used to create retrospective analysis and the construction of a predictive model. In the HCP database, the data gathered from the physicians, third-party audited data aggregators of physician prescribing like IMS, NPA and others and third-party aggregators of audited data of brand drug advertiser promotion activity is used to assess the brand drug use by consumers and, in turn, affect promotional tactic profiles. The data is evaluated by focusing on the different kinds of promotional activities that physicians report as having been directed to them, which allows the brand drug value growth and retention engine software to build a predictive model around the information to assess future behavior of physicians, prescribing changes and prescribing patterns. In the consumer system, the consumer information can be drawn from a wide variety of sources including but not limited to data inputs from consumer behavioral databases like Acxiom, consumer medical record databases, consumer record databases of retail stores, pharmacies, PBMs, wholesalers and switch data companies, among others, which permit the user to plot not only the behavior of consumers but also the optimization of a predictive consumer model, revealing how consumers use or are likely to use a particular brand drug.

One skilled in the art will recognize that the brand value growth and retention system 1 implemented in the cloud computing environment 2 illustrated in FIG. 1 is merely exemplary, and that the embodiments described herein may be practiced and implemented using many other architectures and environments, such as a client-server platform.

Optionally, network security can be added to the cloud system (brand drug value growth and retention system) 1 in the cloud computing environment 2 to make the cloud system 1 secure and compliant. Network security can be enhanced placing a firewall system between the processor/server 16 and the cloud clients 15. Additional network security can also be enhanced using a client-side firewall system on the cloud clients 15. Moreover, the cloud system 1 can employ a backup method in compliance with SAS 70 and HIPAA requirements.

Software Architecture

Figure 2:
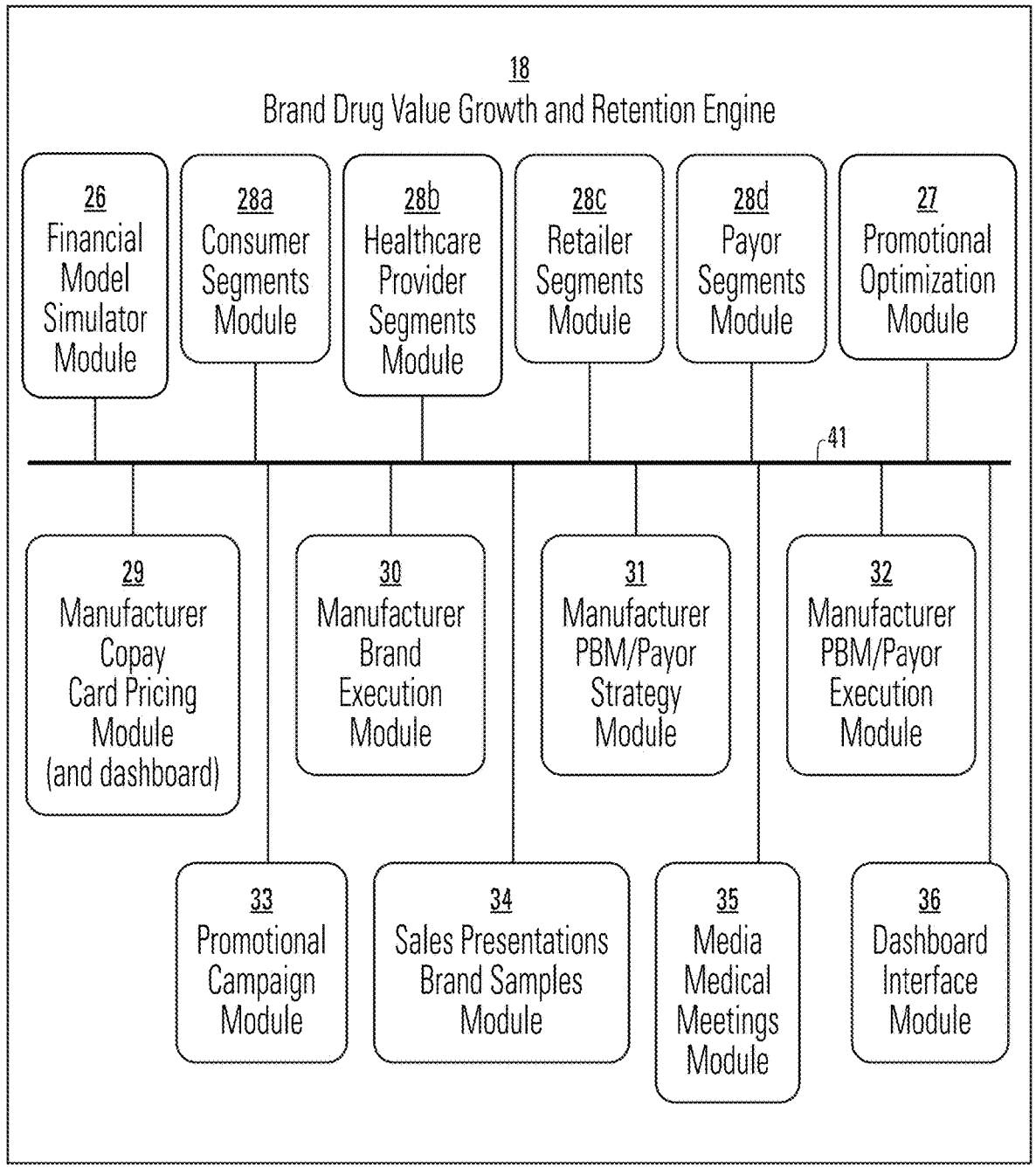
FIG. 2 is a block diagram illustrating one embodiment of a brand drug value growth and retention engine in accordance with the present invention.

FIG. 2 is a block diagram illustrating one embodiment of a brand drug value growth and retention engine 18. The brand drug value growth and retention engine 18 is a comprehensive software tool for optimizing a promotional campaign for a particular brand drug by considering a multitude of data inputs, including consumers, healthcare providers, payors, at least one predictive tool, and a feedback mechanism through a learning machine. The brand drug value growth and retention engine 18 comprises several modules, including the financial model simulator module (and optional dashboard) 26, a consumer segments module 28a, a healthcare segments module 28b, a retailer segments module 28c, a payor segments module 28d, the manufacturer copay card pricing module (optional report and optional dashboard) 29, the manufacturer brand execution module 30, the manufacturer PBM/payor strategy module 31, the manufacturer PBM/payors execution module 32, the promotional campaign module 33, the sales presentations brand samples module 34, the media medical meetings module 35, the dashboard interface module 36, and a bus 41. The payor segments module 28d is configured to provide a predictive module that is used to predict the behavior of consumer and, especially, the predictive behavior around the propensity or likelihood that consumers use a copay card as a secondary source for paying for their medication. The predictive model in the consumer segments module 28a operates to predict when patients desire to use their drugs. For patients who are using the brand drug, the predictive model computes the promotional spending mix in the actual dollar amount of what patients are spending and how patients most effectively spend money around a copay card and other related factors. The healthcare provider segments module 28b is configured to provide a predictive model of promotional activities directed to healthcare providers, which include physicians, nurse practitioners and physician assistants. The manufacturer PBM/payor strategy module 31 is configured to provide a predictive model of behaviors of PBMs, insurance companies, and other payors including government payors. The term "copay card" refers generally and broadly to a consumer loyalty card, which can come in various forms, including digital coupons via a smartphone or a computer, a digital copay card, a traditional copay card, etc.

The financial model simulator module 26 is configured to receive one or more predictive measures from the consumer segments module 28a, healthcare provider segments module 28b, and manufacturer PBM/payor strategy module 31, as well as knowledge from investment decisions that are made by experts to predict brand profitability and cash flows. The output from the tool expresses the incremental brand drug units generated, increment brand drug revenue generated and the incremental profit generated. The financial model simulator module 26 continuously and interactively observes the incoming data associated with a particular copay card and matched control groups of another company's copay card to reveal the promotional output data. The output report will show the profile of a consumer who is most likely to use a copay card. The output report also shows the profile of healthcare providers, specifically those which healthcare providers who use copay cards. The output report will also show which consumers are already on a brand drug or which types of consumers are already on that company's drug, so that a drug manufacturer 6 will not spend money to formulate an advertisement campaign to get these consumers on a copay card because these consumers are already using an identified prescription drug.

Process Flow

Figure 3:
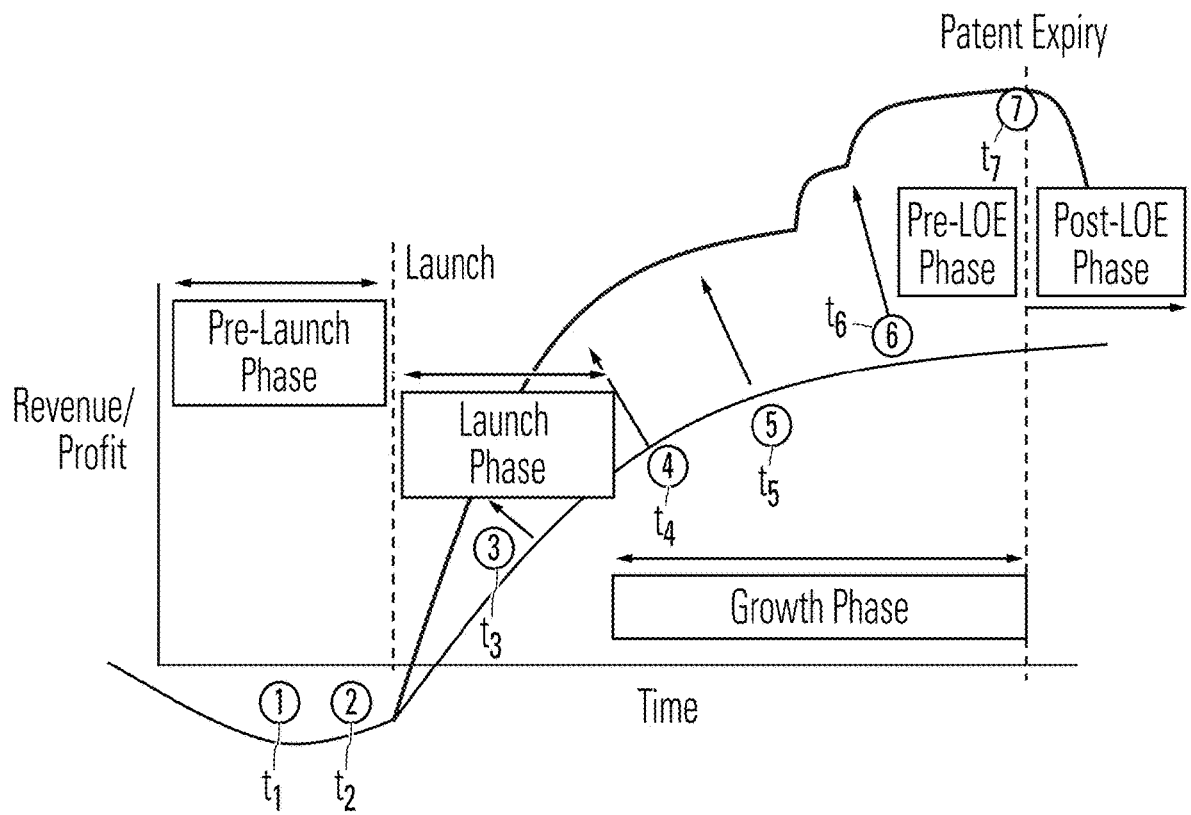
FIG. 3 is a pictorial representation of a brand drug lifecycle with seven key strategies in accordance with the present invention.

FIG. 3 is a pictorial representation of a brand drug lifecycle with seven key strategies. In one embodiment, a successful pharmaceutical company advertiser typically attempts to grow a brand's revenue and profit by applying seven strategies during its lifecycle, with effectiveness measured by revenue and profitability along time dimensions. Initially, a prescription drug manufacturer creates a target product profile at time $t_1$. Once a target product profile has been established, clinical development and market development activities ensue at time $t_2$. Subsequently, at time $t_3$, launch activities are started, which allows the segmentation of potential target consumers. The regional launch of a brand drug positions the brand drug in the launch market based on a selected promotional strategy and execution tactics. Launch of the drug in other regions around the globe generally occurs at time $t_4$ once the clinical development and market development plans for those regions have been completed and the necessary regulatory approvals have been garnered. At time $t_5$, the duration during the launch and growth phases of a brand drug, that consumer experience and engagement with the drug provides valuable data to create more consumer strategies for growing the product. Finally, to grow a brand drug even further, a pharmaceutical company often seeks new claims, indications, formulations and uses through additional clinical trials and new regional regulatory filings at time $t_6$. From target product profile through market development, launch and growth, a brand drug's lifecycle generally reaches its peak sales and later declines during a period in which either a competing drug entry takes market share from the established brand or the patent protection of a brand drug expires leading to its Drug Industry Patent Cliff and its eventual loss of exclusivity in the market at time $t_7$.

Figure 4A:
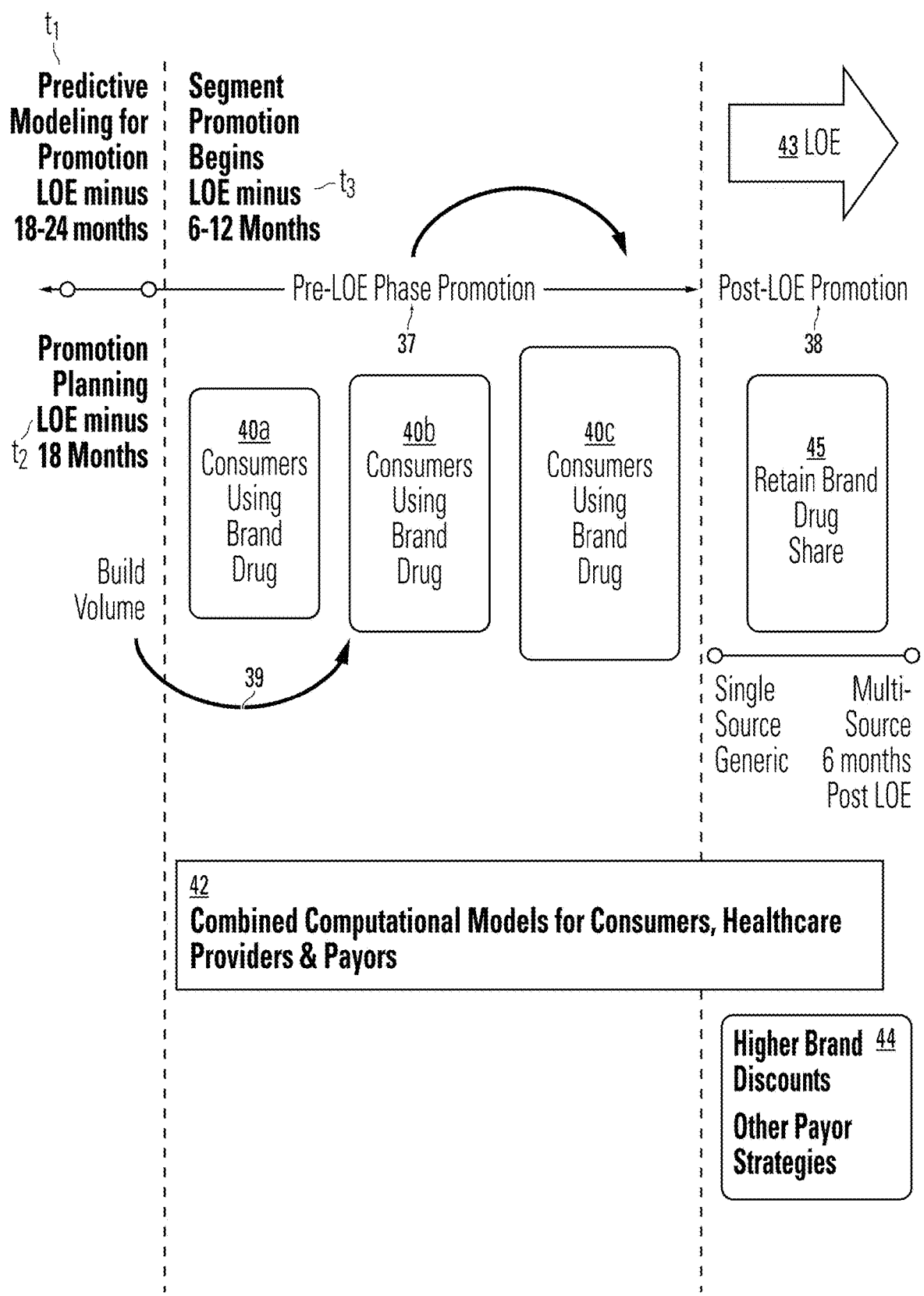
FIG. 4A is a flow diagram illustrating a predictive model of brand drug value growth and retention in pre-LOE and post-LOE phases in accordance with the present invention.

FIG. 4A is a flow diagram illustrating the effect of a predictive model of the brand drug growth, value, a retention engine in pre-LOE period 37 and a post-LOE period 38. The brand strategist 4 formulates a pre-LOE promotional campaign(s) and a post-LOE promotional campaign(s) relative to the patent expiration of a brand drug to generate and retain sales of the brand drug used by consumers prior to and leading up to the period around patent expiration. The application of the brand value growth and retention engine 18 produces the greatest amount of drug brand volume for the least number of promotional campaign dollars and takes into account the following promotional tactics: sales electronic presentations, sales face-to-face presentations, formulary positions, DTC advertising, print advertising, mobile advertising (including smartphones, tablets, and wearable sensors), social network advertising, medical meetings for healthcare professionals, celebrity blogging, samples, reimbursement rates, rebates, discounts, secondary insurance in the form of copay cards, loyalty cards, coupons, vouchers to name just a few.

One embodiment of the overall brand value growth and retention engine 18 comprises a number of key steps as illustrated in FIG. 4 of the present invention. At time $t_1$, which in one example is about 18 to 24 months prior to the brand drug loss of exclusivity, the brand drug value growth and retention engine 18 is configured to generate a predictive model that produces a promotional campaign(s) prior to loss of exclusivity. Time $t_1$ is set by the brand strategist 4.

The predictive model processes a combination of the following data: the computational model of consumer segment data, the computational model of healthcare provider segment data and the computational model of payor segment data. The predictive model identifies correlations that indicate that certain combinations of consumer, healthcare and payor data are predictive. Simultaneously, the brand strategist 4 begins promotional planning at $t_2$ to assure that resources, including dollars, people and processes, are secured to support the implementation of a promotional campaign designed from the output of the predictive model.

If the predictive model indicates the combined data are predictive, the brand strategist 4 then deploys a promotional campaign at time $t_3$ that is comprised of consumer segment promotional plans, healthcare provider segment promotional plans and payor segment promotional plans that are the product of the computational models for consumers, healthcare providers and payors.

In one embodiment, if the predictive model indicates the combined data are not predictive, the output of the predictive model is used to select a different segment promotional plan modified for a specified segment within a target consumer group for feeding back iteratively to the computational model of consumer segment data, the computational model of healthcare provider segment data and the computational model of payor segment data for further optimization until a combination of data is deemed by the predictive model to be predictive.

Given that consumers, healthcare professionals and payors have changing needs, wants, demands and behaviors, in the embodiment in FIG. 4 the application of the brand value growth and retention engine 18 continuously operates and optimizes promotional campaigns until the brand strategist 4 determines that he or she no longer desires to promote the brand drug in the market. In the embodiment as shown in FIG. 4, the application of the brand value growth and retention engine 18 continues for the finite post-LOE phase 38 of the brand drug. In this embodiment the predictive model produces various promotional campaigns that are generated based on segment promotional plans that are optimized from $t_1$ through the period when multiple generics enter the market during the finite post-LOE phase of the brand drug in the market.

The predictive model determines segment promotional plans and which promotional tactic profiles require adjustment to yield a higher response rate at a certain investment level over time and therefore a promotional campaign relies on the learning machine in the predictive model to reveal which segment promotional plans are optimized or not optimized.

The brand drug value growth and retention engine 18 is configured to generate an optimal segment promotional plan(s) from the computation model segment data that are combined and processed through the predictive model to generate a promotional campaign at time $t_3$ prior to the loss of exclusivity based on the predictive model produced at time $t_1$.

One objective is to find correlations between a promotional tactic profile and prescribing levels of a brand drug by physician segments. Promotional tactics can include the number of brand sales presentations made to a doctor, the number of medical meetings that the physician attended, the number of brand samples that were provided to a doctor, and the number of copay cards provided to a doctor, among others. The optimal segment promotional plan(s) in a promotional campaign have tactic profiles that are directed to consumers, healthcare providers, and payors. In some instances, the computational models are run iteratively until there is sufficient data, and the predictive model is sufficiently developed to deem the output predictive. After the predictive model is deemed predictive, the overall promotional campaign will most likely have the highest impact, which provides the highest brand drug volume for the least amount of promotional dollars.

Even after the promotional campaign has been launched, the predictive model continues to operate, continues to receive new data, and continues to refine and modify the parameters of the predictive models. A curve 39 represents the iterative and continuous running of predictive models to refine, modify, transform and improve an optimal promotional campaign, which over time is intended to increase the sales of brand drugs used by the consumers, as shown in a first population of consumers using brand drug 40a, a second population of consumers using brand drug 40b that is larger than the first population size, and a third population of consumers using brand drug 40c that is larger than the second population size.

To better select a tactic profile, to which a consumer 7 may be more responsive, the brand strategist 4 attempts to understand the segments of consumers including their needs, wants, demands and behaviors. Depending on what a particular segment of consumers will respond to, the brand strategist 4 selects effective consumer segment promotional plans, which, combined with healthcare provider segment promotional plans and payor segment promotional plans, constitute a brand drug promotional campaign by operating through a predictive model at 42. Similarly, the brand drug value growth and retention engine 18 is configured to collect computational model data from physician segments, analyzing physician prescribing behavior, and analyzing the data relative to the promotional tactics a drug manufacturer 6 has deployed against a particular physician. Additional considerations can include sales calls from sales representatives and the number of educational programs that physicians attend. Similarly, the brand drug value growth and retention engine 18 is configured to collect computational model data from payor segments, analyzing payor behavior, and analyzing the data relative to the promotional tactics (including pricing and discounting) a drug manufacturer 6 has deployed against a particular payor.

Modified promotional tactics producing different segment promotion plans begin at time $t_3$, which in one embodiment of the present invention is a time duration closer to the loss of exclusivity relative to $t_1$ and $t_2$. A promotional campaign comprises a plurality of segment promotional plans. Each segment promotional plan is directed to a particular segment of consumers, a particular segment of healthcare providers and/or a particular segment of payors with specific tactics to which a respective segment responds. Different segments of consumers, segments of healthcare providers and segments of payors may have the same or different sets of promotional tactics that are applied in order to have the predictive model produce an effective promotional campaign.

In one embodiment, the brand value and retention engine 18 is configured to optimize promotion at the time of loss of exclusivity. A brand drug company may significantly increase its brand drug direct to consumer advertising including but not limited to TV advertising, print advertising, copay cards, loyalty cards, coupons etc. This is done through several different promotional channels, including, but not limited to, electronic mail, physical mail, video push, mobile device advertising and the use of copay cards. The aim in this embodiment is to encourage consumers to speak to their doctors about starting therapy on a brand drug or to remain loyal to brand drugs that they have been using. The increase in direct to consumer advertising is intended to retain more consumers on the brand drug and thus increase and retain brand drug volume before the loss of exclusivity, after the loss of exclusivity even months after the loss of exclusivity.

While not available to all drugs, sometimes a brand drug will be designated as one that is granted the legal rights to have only one competing single source generic drug at the time of loss of exclusivity of the brand. This designation would have occurred early in the brand's life.

A brand drug is typically price discounted immediately after the drug's loss of exclusivity 43 so the brand drug can remain price competitive with the single or other available generic drugs. Therefore, if a consumer 7 views the brand drug and the generic drug to be comparable in price and effectiveness and safety, they are more likely to be open to remaining on the branded drug after loss of exclusivity.

The negotiation for brand formulary position and pricing 44 with PBMs 8 is another key factor to ensure patients can get access to the branded drug before and after the loss of exclusivity. To ensure the PBM 8 patients have access to the brand, manufacturers negotiate arrangements that provide brand drugs at discounted prices to remain price competitive with generic drugs. Without such negotiated arrangements, a PBM may automatically switch patients from the brand drug to a generic drug upon the expiration of the exclusivity period. For example, the price of a brand drug could decrease by 20% to 30% relative to the price before the loss of exclusivity period in order to remain price competitive with a generic drug at 45, which the population size of the consumers is reduced relative to the third population size of consumers using the brand drug.

Often market share of the brand drug will fall after the loss of exclusivity. A drug manufacturer aims to retain significant market share up to and post loss of exclusivity. In time, multiple sources of generic drugs will often come to one market, which will place growing price pressure on expired brands s and can cause the manufacturer to continue to reduce the price of the brand drug to remain competitive with generics.

Figure 4B:
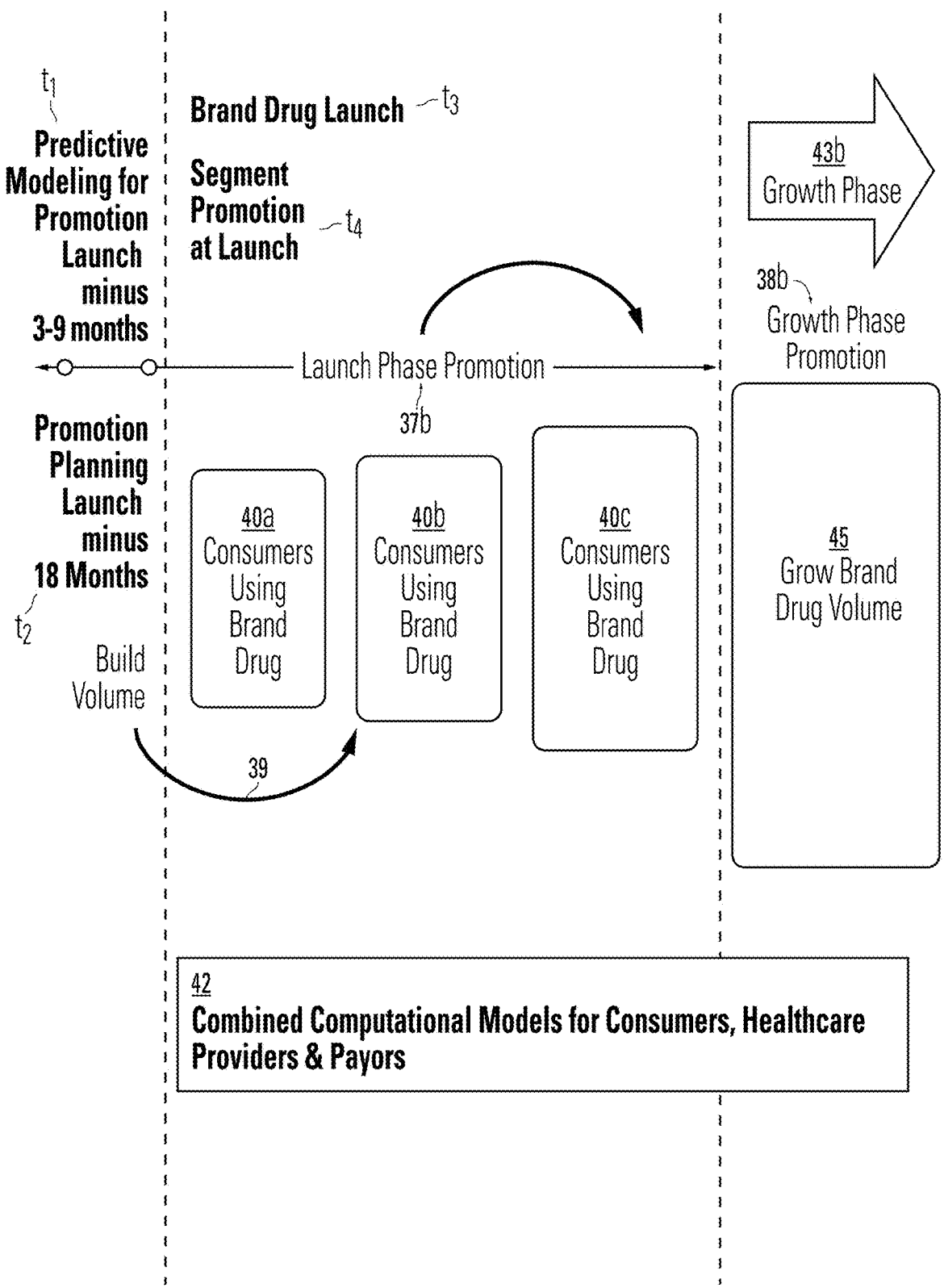
FIG. 4B is a flow diagram illustrating a predictive model of brand drug value growth and retention in the launch phase of a brand drug in accordance with the present invention

FIG. 4B is a flow diagram illustrating the effect of a predictive model of the brand drug growth, value, a retention engine in launch phase of a brand drug. The brand strategist 4 formulates a launch promotional campaign(s) to generate and retain brand drug use at launch and post launch and prior to a brand's growth phase. The application of the brand value growth and retention engine 18 produces the greatest amount of brand drug sales for the least amount of promotional campaign dollars and takes into account the following promotional tactics: sales electronic presentations, sales face-to-face presentations, formulary positions, DTC advertising, print advertising, mobile advertising (including smartphones, tablets, and wearable devices), social network advertising, medical meetings for healthcare professionals, celebrity blogging, samples, reimbursement rates, rebates, discounts, secondary insurance in the form of copay cards, loyalty cards, coupons to name just a few.

One embodiment of the overall brand value growth and retention engine 18 comprises a number of key steps as illustrated in FIG. 4B of the present invention. At time $t_1$, which in one example is about 3 to 9 months prior to the brand drug, the brand drug value growth, and retention engine 18 is configured to generate a predictive model that produces a promotional campaign(s) for use at the time of brand launch. Time $t_1$ is set by the brand strategist 4.

The predictive model processes a combination of the following data: computational model of consumer segment data, the computational model of healthcare provider segment data and the computational model of payor segment data. The predictive model identifies correlations that indicate that certain combinations of consumer, healthcare, and payor data are predictive. Simultaneously, the brand strategist 4 has begins promotional planning at $t_2$ to assure that resources, including dollars, people, and processes, are secured to support the implementation of a promotional campaign designed from the output of the predictive model.

If the predictive model indicates the combined data are predictive, the brand strategist 4 then deploys a promotional campaign at time $t_3$ that is comprised of consumer segment promotional plans, healthcare provider segment promotional plans and payor segment promotional plans that are the product of the computational models for consumers, healthcare providers and payors.

In one embodiment, if the predictive model indicates the combined data are not predictive, the output of the predictive model is used to select a different segment promotional plan modified for a specified segment within a target consumer group for feeding back iteratively to the computational model of consumer segment data, the computational model of healthcare provider segment data and the computational model of payor segment data for further optimization until a combination of data is deemed by the predictive model to be predictive.

Given that consumers, healthcare professionals and payors have changing needs, wants, demands and behaviors, in the embodiment in FIG. 4B the application of the brand value growth and retention engine 18 continuously operates and optimizes promotional campaigns until the brand strategist 4 determines that he or she no longer desires to promote the brand drug in the market. In the embodiment as shown in FIG. 4B, the application of the brand value growth and retention engine 18 for the brand drug launch phase continues for the launch phase 37b of the brand drug. The launch phase is defined by the brand strategist. In this embodiment the predictive model produces various promotional campaigns that are generated based on segment promotional plans that are optimized from $t_1$ through the period when the brand strategist determines that the launch phase of the brand drug has concluded.

The predictive model determines segment promotional plans and which promotional tactic profiles require adjustment to yield a higher response rate at a certain investment level over time and therefore a promotional campaign relies on the learning machine in the predictive model to reveal which segment promotional plans are optimized or not optimized.

The brand drug value growth and retention engine 18 is configured to generate an optimal segment promotional plan(s) from the computation model segment data that are combined and processed through the predictive model to generate a promotional campaign at time $t_3$ launch phase based on the predictive model produced at time $t_1$.

One objective is to find correlations between a promotional tactic profile and prescribing levels of a brand drug by physician segments. Promotional tactics can include the number of brand sales presentations made to a doctor, the number of medical meetings that the physician attended, the number of brand samples that were provided to a doctor, and the number of copay cards provided to a doctor, and among others. The optimal segment promotional plan(s) in a promotional campaign have tactic profiles that are directed to consumers, healthcare providers, and payors. In some instances, the computational models are run iteratively until there is sufficient data, and the predictive model is sufficiently developed to deem the output predictive. After the predictive model is deemed predictive, the overall promotional campaign will most likely have the highest impact, which provides the highest brand drug sales for the least amount of promotional dollars. Even after the promotional campaign has been launched, the predictive model continues to operate, continues to receive new data, and continues to refine and modify the parameters of the predictive models. A curve 39 represents the iterative and continuous running of predictive models to refine, modify, transform and improve an optimal promotional campaign, which over time is intended to increase the volume brand drugs used by the consumers, as shown in consumers in first population size using brand drug 40a, consumers in a second populations size using the brand drug 40b with a second population size that is larger than the first population size, and consumers in a third population size using brand drug 40c with a third population size that is larger than the second population size.

To better select a tactic profile, which a consumer 7 may be more responsive, the brand strategist 4 attempts to understand the segments of consumers including their needs, wants, demands and behaviors. Depending on what a particular segment of consumers will respond to, the brand strategist 4 selects effective consumer segment promotional plans, which combined with healthcare provider segment promotional plans and payor segment promotional plans, constitute a brand drug promotional campaign by operating through a predictive model at 42. Similarly, the brand drug value growth and retention engine 18 is configured to collect computational model data from HCP segments, analyzing HCP prescribing behavior, and analyzing the data relative to the promotional tactics, a drug manufacturer 6 has deployed against a particular physician. Additional considerations can include sales calls from sales representatives and the number of educational programs that physicians attend among other promotional tactics. Similarly, the brand drug value growth and retention engine 18 is configured to collect computational model data from payor segments, analyzing payor behavior, and analyzing the data relative to the promotional tactics (including pricing and discounting) a drug manufacturer 6 has deployed against a particular payor.

Modified promotional tactics producing different segment promotion plans. A promotional campaign comprises a plurality of segment promotional plans. Each segment promotional plan is directed to a particular segment of consumers, a particular segment of healthcare providers, and/or a particular segment of payors with specific tactics to which a respective segment responds. Different segments of consumers, segments of healthcare providers, and segments of payors may have the same or different sets of promotional tactics that are applied in order to have the predictive model produce an effective promotional campaign. In one embodiment, the brand value and retention engine 18 is configured to optimize promotion at the time launch. A brand drug company may launch a brand drug with very high spending aimed at direct to consumer advertising including but not limited to TV advertising, print advertising, copay cards, loyalty cards, coupons etc. This is done through several different promotional channels, including but not limited to, electronic mail, physical mail, video push, mobile device advertising and the use of copay cards. The aim in this embodiment is to encourage consumers to speak to their doctors about starting therapy on a brand drug or switching from another brand drug that they have been using. The increase in direct to consumer advertising is intended to capture more consumers on the brand drug and thus increase brand drug volume during the launch phase.

The negotiation for brand formulary position and pricing 44 with PBMs 8 is another key factor to ensure patients can get access to the branded drug at launch. To assure the PBM 8 patients have access to the brand, manufacturers negotiate arrangements that provide branded drug at discounted prices to remain price competitive with other branded drugs. Often without such negotiated arrangements, a PBM may automatically deny its patients access to the brand drug at launch, instead requiring patients to use cheaper brand drugs or generics.

Figure 5:
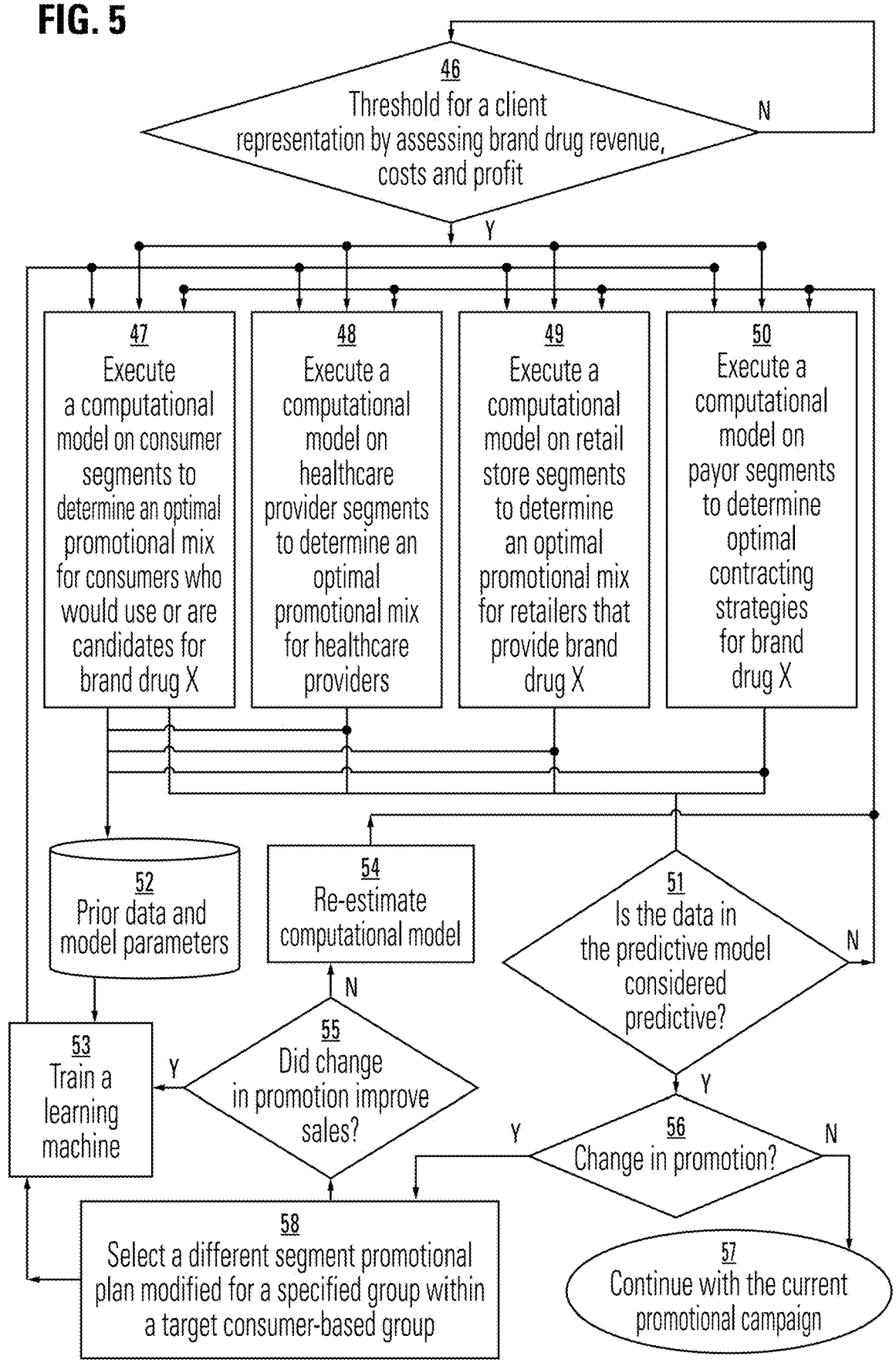
FIG. 5 is a flow diagram illustrating a first embodiment of a predictive model method in brand drug value growth and retention in accordance with the present invention.

FIG. 5 is a diagram illustrating one embodiment of a predictive model method executed by the brand drug value growth and retention engine 18. At step 46, the brand drug value growth and retention engine 18 is configured to determine a predefined or computed threshold for a prospective brand. The threshold for a prospective brand engagement, in one embodiment, can be dictated by time to LOE, a competitive market, brand revenue, brand marketing spending, and brand profit. If the prospective brand does not meet the threshold, the process remains at step 46. Upon meeting the threshold for a brand engagement, the brand drug value growth and retention engine 18 proceeds to execute a computational model on consumer segments in step 47, execute a computational model on healthcare provider segments in step 48, and execute a computational model on payor segments in step 50. Steps 47, 48, 49, 50 can occur in parallel or in some combination in this embodiment of the present invention. At step 47, the consumer segments module 28a is configured to run a computational model on consumer segments to determine an optimal promotional plan for consumers who are candidates for a particular brand drug. The computational models on consumer segments are built based on various attributes of individual consumers or subgroups including but not limited to the consumer's use of copay cards, their medical conditions, prior prescription brand drug purchases, prior OTC brand drug purchases, insurance carriers, preferred retail stores, their buying patterns, shopping patterns, income levels, gender, race, educational levels, among others. The number and types of attributes in a computational model of consumer segments are dependent and can be adjusted based on several factors including but not limited to a set of predetermined attributes at the outset of a promotional campaign, modifying the attributes from a source during a promotional campaign, the result of a predictive model, or the output from the learning machine.

At step 48, the healthcare provider segments module 28b is configured to run a computational model on healthcare providers who treat consumers are users or who are candidates using the particular brand drug. In this embodiment, the term healthcare provider segments refers to optimizing individual healthcare providers or subgroups within segments as a segment, rather than by geographical segmentation. At step 49, the healthcare provider segments module 28b is configured to run a computational model on individual or subgroups of retail segments to determine an optimal promotional mix for retailers that provide the brand drug (or drug brand X) to consumers.

At step 50, the manufacturer PBM/payor strategy module 31 and manufacturer PBM/payors execution module 32 are configured to run a computational model on individual or subgroups of payor segments, such as PBMs and insurers, to determine optimal contracting strategies for the particular brand drug. Data intelligence for selecting a particular promotion campaign can be sourced from the computational model on consumer segments at step 47, the computational model on healthcare provider segments at step 48, and the computational model of payor segments at step 50. The promotional campaign is not only based on the costs of advertising, but it also considers formulary position and the related pricing associated with a brand's formulary position, pricing for a brand manufacturer and the optimal pricing for patients by considering the different promotional mixes for consumers and individual healthcare providers and by matching that to an optimizing rebating and discounting strategy.

In one embodiment, pertaining to formulary positions, a PBM may make available a number of prescription drugs intended to treat a specific disease or disorder. The PBM may allow one of the drugs to be widely available to their patients because of the negotiated rebates and discounts extended by the manufacturer and the broad benefits determined by the PBM medical authorities. In this embodiment, the PBM may require no insurance copay for this drug as a way to encourage physicians and patients to use this preferred drug. As an alternative to the preferred drug, alternative drugs may be made available with different rebates and discounts. For these drugs, patients may be charged an insurance copay or may have to pay for the full cost of the drug with no contribution from their insurance company. The different levels of rebates, discounts, and copay pricing provide different variables to produce an optimal brand drug formulary position.

At step 51, the financial model simulator module 26 in the brand value and retention engine 18 is configured to compute and generate a combination predictive model in this embodiment. The financial model simulator module 26 receives the computational model on consumer segments from step 47, the computational model on healthcare providers segments from step 48, the computational model on the retail store segments from step 49, and the computational model on payor segments in step 50 to run a predictive model of these input data to generate an optimal promotional campaign for the specified brand drugs. Data received by the financial model simulator module 26 should be sufficiently large to make the predictive model meaningful. Continuous streams of consumer segment data, healthcare provider data and payor segment data are fed into the predictive model. In some embodiments, the predictive model is computed based on receiving two or more computational models from among the four possible computational models, i.e., the consumer segments model in step 47, the healthcare provider segments computational model in step 48, the retail store segments computational model in step 49, and the payor segments computational model in step 50. In other embodiments, the predictive model is computed based on receiving one or more computational models from among the four possible computational models in steps 47, 48, 49, 50.

In some embodiments, the predictive model combines various computational models are executed in a way that is complaint with present government regulations, like HIPPA, or future government amendments or legislations.

At step 52, the brand value growth and retention 18 stores, accumulates and retrieves prior promotional campaigns and their results, for both promotions of different earlier products and any prior campaigns and their results for the current product.

At step 53, the brand drug value growth and retention engine 18 is configured to invoke machine learning methods in real time or recent data to estimate and attempt to optimize the parameters for prediction of one or a plurality of computational models such as those in steps 47, 48, 49, 50. The specifics of the implementation of machine learning methods employed are known in the literature. For additional information on the machine learning methods, see Michalski, R., J. Carbonell, and T. Mitchell (1986), *Machine Learning: An Artificial Intelligence Approach*, Volume II, Morgan Kaufman Publishers: Los Angeles; Bishop, C. M. (2006), *Pattern Recognition and Machine Learning*, Springer; Singh, Y., P. K. Bhatia, O. Sangwan (2007), *A Review of Studies of Machine Learning Techniques*, International Journal of Computer Science and Security, Volume (1): Issue (1), 70-84, which are incorporated by reference as if fully set forth herein. Machine learning methods may include, for example, logistic regression, support vector machines, decision trees, random forests, max-entropy classifiers, re-enforcement learning, genetic algorithms, neural networks or other known or new methods. Most of these methods are based on Bayesian statistics and use prior data (e.g. prior campaigns) and prior results (e.g. failure, success, degree of partial success) of said prior data (e.g. campaigns or individual tactics within the campaigns) to improve the weights and other parameters in the predictive models. For additional information on specifics of Bayesian statistics, see Spiegelhalter D. and K. Rice (2009), *Bayesian statistics*, Scholarpedia; Bolstad, W. (2007), Introduction to Bayesian Statistics, 2nd Ed., John Wiley & Sons: New Jersey; Bishop, C. M. (2006), *Pattern Recognition and Machine Learning*, Springer, which are incorporated by reference as if fully set forth herein.

Step 53 may also include active or proactive learning where a new tactic or new campaign (e.g. advertising via social media such as Facebook, or via mobile apps on smartphones) may be tried in order to jointly optimize both new knowledge gained about the effectiveness of the new campaigns or tactic and the immediate impact of the selected campaigns and tactics. The former may be viewed as longer-term or amortized benefit, whereas the latter is the current benefit predicted by the computational model(s). Proactive learning takes into account the cost and risk of experimental campaigns, and this would be a novel application area for such machine learning systems. For additional information on specifics of active or proactive learning, see B. Settles (2012), Active Learning: Synthesis Lectures on Artificial Intelligence and Machine Learning, Morgan & Claypool; Donmez, P., Carbonell, J. (2008), "Proactive Learning: Cost-Sensitive Active Learning with Multiple Imperfect Oracle," in *Proceedings of the 17th ACM Conference on Information and Knowledge Management* (CIKM '08), Napa Valley; Donmez, P. and Carbonell, J. (2008), "Optimizing Estimated Loss Reduction for Active Sampling in Rank Learning," in *Proceedings of the International Conference in Machine Learning*, which are incorporated by reference as if fully set forth herein.

At step 54, the brand drug value growth and retention engine 18 is configured to allow for re-estimating one or more computational models if their results were not positive. For instance, if the machine learning method suggested two potential but mutually exclusive improvements, one of which was attempted without positive results, the computational model may then be re-estimated with the second improvement and fed back into the overall system.

At step 55, the brand drug value growth and retention engine 18 is configured to determine the benefit (e.g. improvement in sales) of the promotional campaign and feeds back to the learning machine (step 53) directly if positive to re-enforce, or indirectly via step 54 (re-estimation), and re-runs the computational models to inform the learning machine that certain predictions need revision.

Figures 6A, 6B:
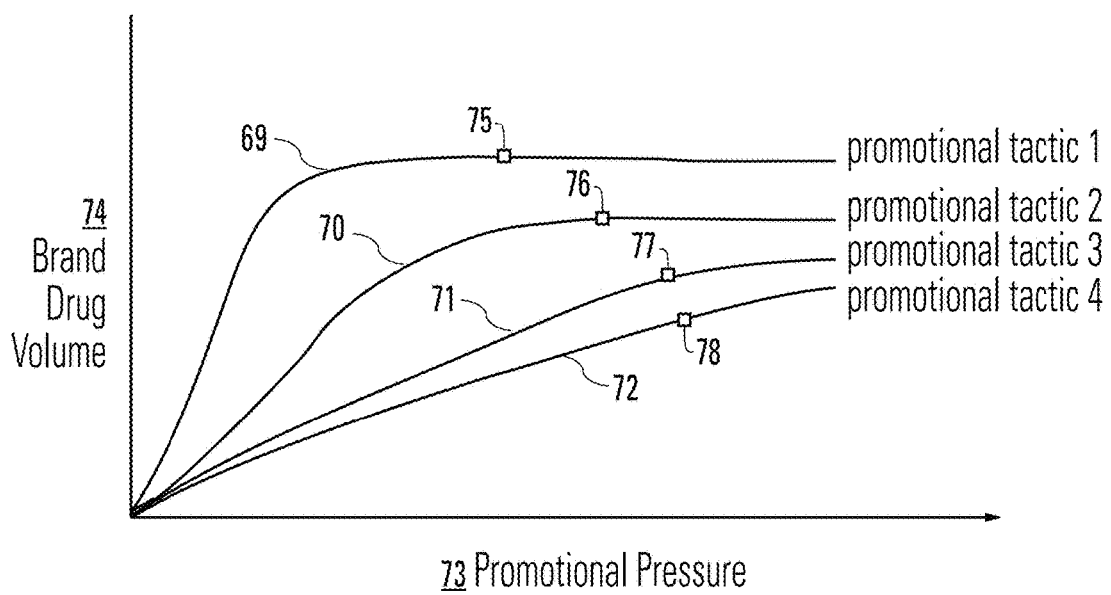
FIG. 6A is a table illustrating a promotional campaign from a collection of segment promotional plans in accordance with the present invention.
FIG. 6B is a graphical curve illustrating different promotional tactics in accordance with the present invention.

As an example of a promotional campaign, FIG. 6A is a table illustrating a promotional campaign from a collection of segment promotional plans, represented in this embodiment as a table 59 stored in a database. The table 59 comprises vertical columns on different segments 60 of consumers (or segments of healthcare providers). The horizontal rows denote different promotional tactics 61 directed to the consumer segments 60. For the first consumer segment 62, among the different promotional tactics 61 from 1 to n as applied to the first consumer segment 62, the first consumer segment 62 responds well to the second tactic profile 63b, the third tactic profile 63b, and the seventh tactic profile 63c. The identified promotional tactics 63a, 63b, 63c, which have been determined to be effective promotional tactics directed to the first consumer segment 62, are collectively referred to as a first segment promotional plan SPP1 64. The brand drug value growth and retention engine 18 is configured to determine the number of tactic profiles that are effective against a particular consumer segment, resulting in a series of segment promotional plans: SPP1 64 for the first consumer segment, SPP2 66 for the second consumer segment, SPP3 67 for the third consumer segment, and SPPn 68 for the n consumer segment. A promotional campaign 65 comprises a plurality of segment promotional plans, represented by the following equation where timing of segments is regulated by the function $\alpha(t_i)$, where in one embodiment the function can be a sequence, in another all in parallel, and in other embodiments any partially or fully sequential or parallel segments:

$$PC = \sum_{i=1,N} \alpha(t_i) SPP_i$$

In one embodiment, the promotional campaign may include explicit interaction terms among the actual or planned segment promotional plans as well as individual segment promotional plans (SPPs). The explicit interaction terms can be binary, comprising any planned or actual SPP interacting with any other planned or actual SPPs. The terminology "explicit interaction terms" may refer to a term that combines two or more variables in a potentially non-linear way, e.g. $G(X_1, X_2)$, especially if used inside another equation, such as an otherwise linear equation on $X_1$ and $X_2$ is an explicit interaction term between $X_1$ and $X_2$. The function G can be anything meaningful in the application area. For instance, G can be a product $X_1 * X_2$ or a ratio $X_1/X_2$, or something such as a transformed sum, e.g. $LOG(X_1) + LOG(X_2)$. For example, the magnitude of one campaign element may be three times larger than that of a different campaign element, e.g. $G(C1, C2) = Cost(C1)/Cost(C2) = 3$, without having to specify the actual value of either $Cost(C1)$ of $Cost(C2)$, just their relative magnitudes.

Returning to step 51 in FIG. 5, the financial model simulator module 26 is configured to compute a segment promotional plan by considering several key variables, including coefficients, promotional tactics, segments and frequency. In one formulation, each tactic profile in a particular segment promotional plan is determined by the weighted factors of the coefficients multiplied by the frequency in which the tactic is displayed for a particular segment as represented by the following equation:

$$SPP = \sum_{i=1,m} \alpha(t_i) \beta_i T_i (F_i, S_j)$$

where $\beta_1 * T_1(F_1, S_j)$ denotes the first tactic profile, $\beta_2 * T_2(F_2, S_j)$ denotes the second tactic profile, $\beta_3 * T_3(F_3, S_j)$ denotes the third tactic profile, and so on up to the $n^{th}$ tactic profile, where n is the total number of profiles. The coefficients $\beta_i$ are weighted factors applying respectively to the first tactic profile, the second tactic profile and the third tactic profile. The first term, $\beta_i * T_1(F_1\ S_j)$, represents the frequency $F_1$ in applying the first promotional tactic $T_1$ to a first consumer segment $S_j$. The second term, $\beta_2 * T_2(F_2, S_j)$, represents the frequency $F_2$ in applying the second promotional tactic $T_2$ to first consumer segment $S_i$ and so on up to the $m^{th}$ tactic, where m is the total number of tactics. The $\alpha(t)$'s again denote any ordering or parallelizing temporal function. Although, for simplicity, the equation is presented as a summation, which is only one embodiment of the invention; the summation may be replaced by any other constructive combination function. Tactic profiles may indicate any manner of promotion, including but not limited to traditional media, social media, consumer-direct and payor direct programs.

If the result of the predictive model is negative, the process returns to steps 47, 48, and 50 for conducting real time or recent data predictive analysis. If the financial model simulator module 26 determines that the data is considered predictive, then at step 56 the brand drug value growth and retention engine 18 is configured to determine if a change in promotional campaign is desired at this time. The current promotional campaign continues if there are no changes in the promotional campaign, as is shown in step 57. However, if a change in a promotional campaign is desired, the brand drug value growth and retention engine 18 is configured to select a different promotional campaign for a specified segment within a targeted consumer-based group at step 58. At step 53, the brand drug value growth and retention engine 18 continuously trains a learning machine as a feedback mechanism to improve and optimize the predictive model of promotional campaigns.

Figure 7:
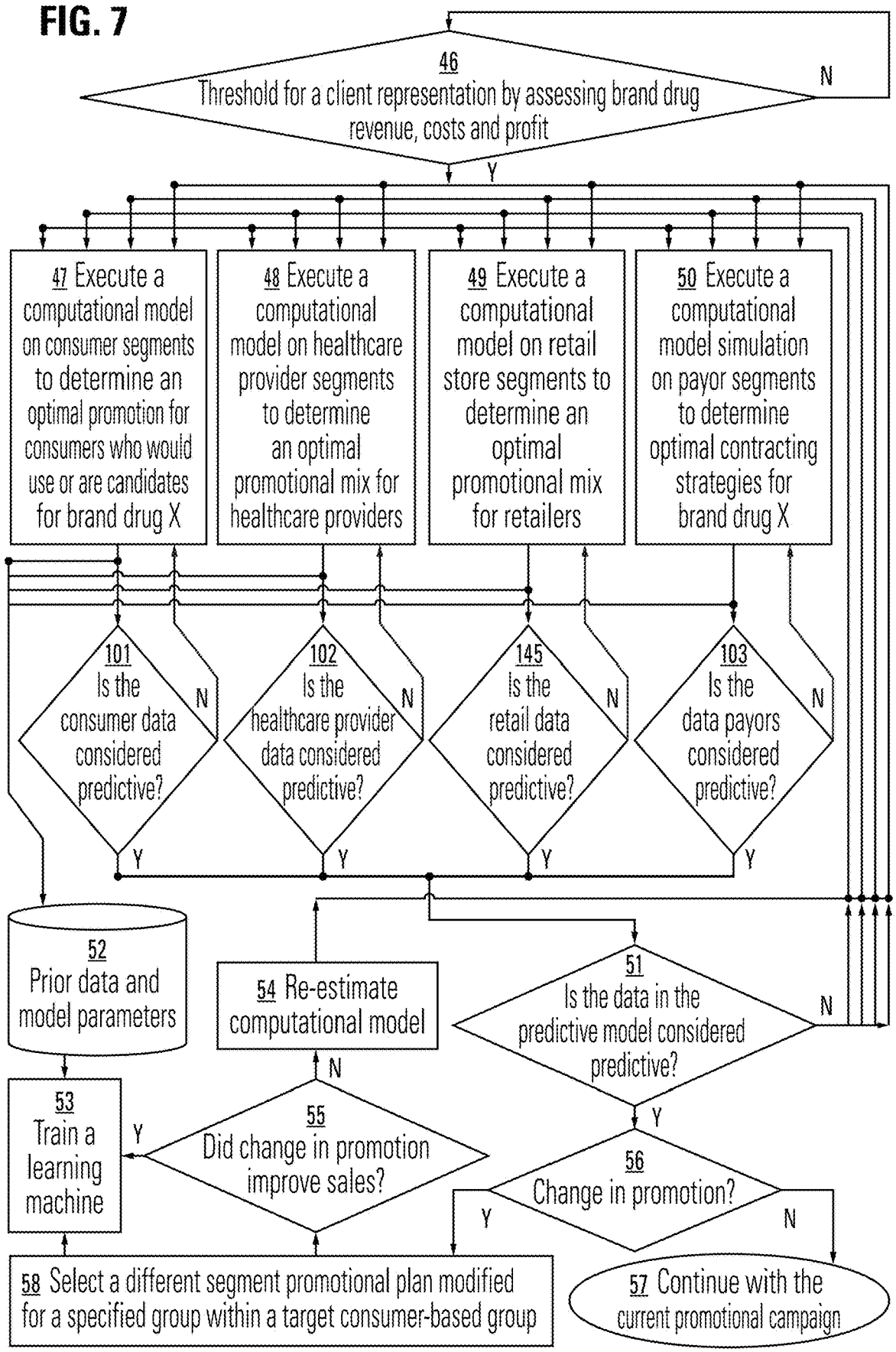
FIG. 7 is a flow diagram illustrating a second embodiment of a predictive model method in brand drug value growth and retention in accordance with the present invention.

In an alternative embodiment as shown in FIG. 7, the predictive model method can be a cumulative predictive model at step 51 based on an individual predictive model, which the financial model simulator module 26 is configured to determine whether the consumer data is predictive at step 101, whether the healthcare provider data is predictive at step 102, and whether the payor segment data is predictive at step 103. This formulation can be represented mathematically by the following equation:

$$\text{Cumulative Predictive model} = F(P(M_C), P(M_{HCP}), P(M_P), P(M_R))$$

where $P(M_C)$ denotes the predictive model consumer segment data in step 101, $P(M_{HCP})$ denotes the predictive model of healthcare provider segment data in step 102, $P(M_P)$ denotes the predictive model of payor segment data in step 103, and $P(M_R)$ denotes the retail-sales-based predictive model in step YYY. For example, the predictive model would evaluate a run on 30 segments of patients, 30 segments of physicians, and 15 possible rebating structures. The function F is any combination function and in its simplest embodiment would be additive, e.g. a weighted sum.

In one embodiment the predictive model uses data from retail sales of pharmaceutical products gathered from consumers with affinity cards at pharmacies or other retail outlets. This data is typically normalized to account for the fraction of the population that uses affinity cards in each major geographical region or with each large-scale retailer, and for other factors (age differences, health plans, etc.). This predictive model based on actual sales is then used to estimate trends (e.g. increased sales of certain products or product categories, seasonal variations, etc.), and these trends plus current values are used to estimate the expected sales. A more complex embodiment would include the effects of marketing efforts combined with baseline trend prediction. The prediction in such an embodiment may be estimated by the following function or by other methods of combining similar information:

$$P(M_R) = \sum_{X_i \in R} N(X_i)\, \text{Sales}\,(X_i)\left(1 + \frac{d(\text{Sales}\,(X))}{dt}\right)$$

In the above function we have a set of retail products R={$X_1$, $X_2$, . . . . $X_n$}, measured sales volume of each $X_i$, normalization $N(X_i)$ to account for the expected fraction of sales actually recorded (N=the inverse of that fraction), and adjusting for increasing or decreasing trends as measured over a time interval t.

In one embodiment, the predictive model combines information from computational models of the consumer segment data, healthcare provider segment data, the retail segment data and the payor segment data in a linear manner or a substantially linear manner. The combined information in the predictive model provides explicit weights to one or more components in the combined information. The term "linear" is commonly used in the art and may refer to the elements (variables, components, sub-components) that are combined via an additive process, possibly with weights. The term "substantially linear" refers to a linear equation that could still have a small corrective factor that may be non-linear. For instance, a linear combination of variables $X_1$ $X_2$, $X_3$, and $X_4$ can be represented mathematically by $Y = A_1 X_1 + A_2 X_2 + A_3 X_3 + A_4 X_4$, where $A_1$ is a coefficient (a weight) assigned to $X_1$, $A_2$ is a coefficient for $X_2$, $A_3$ is a coefficient for $X_3$, and $A_4$ is a coefficient for $X_4$. Explicit weights are the A1, A2, A3, A4 above, i.e. the coefficients.

In some embodiments, the predictive model in step 51 is computed based on receiving two or more computational models from among the four possible computational models, i.e., the consumer segments model in step 47, the healthcare provider segments computational model in step 48, the retail store segments computational model in step 49, and the payor segments computational model in step 50. To phrase it in another way, the predictive model in step 51 is computed based on receiving two or more predictive elements from among the four possible predictive elements, i.e., the predictive element for the consumer segments model in step 101, the predictive element for the healthcare provider segments computational model in step 102, the predictive element for the retail store segments computational model in step 145, and the predictive element for the payor segments computational model in step 103. In other embodiments, the predictive model is computed based on receiving one or more computational models from among the four possible computational models in steps 47, 48, 49, 50, or receiving one or more predictive elements among the four predictive elements in steps 101, 102, 145, 103.

Embodiments of the present invention include a promotion campaign that is represented by the following augmented equation, where j=1, M ranges over all segment promotional plans, including those of other active or planned promotion campaigns and the function $g(SPP_i, SPP_j)$ computes interactions among the campaign plan portions if any:

$$PC = \sum_{j=1,M} \sum_{i=1,N} \alpha(t_i)[SPP_i + g\,(SPP_i,\, SPP_j)]$$

For example, two promotional campaigns for the same medication may interact. For instance, their message should normally be consistent, e.g. "more effective treatment" (vs "cheaper" vs "easier to take"). Alternately, two concurrent campaigns for different medications may be optimized by combining promotion plan segments. For instance, the same mailing may contain two fliers for treating age-related ailments and state that medications may be taken together—e.g. an anti-inflammatory and a skin-rejuvenation ointment. Alternatively, two drugs for the same ailment may confuse the market, and therefore they should not be promoted simultaneously. These examples are meant to be illustrative and not limiting as to the range of possible positive and negative interactions among promotion campaigns (PCs) and their segment promotional plans (SPPs). The function g(SPPi, SPPj) computes the interaction and can have a positive value (e.g. cost savings by combining mailings) or a negative value (e.g. two statin drugs promoted in parallel campaigns targeted at the same consumers, confusing them). Thus, g modulates the campaigns in order to optimize their combination, not just each campaign independently. In some embodiments, the promotional campaign PC is a weighted combination of the segment promotional plans (SPPs). The term "weighted combination" may refer to "linear" and implies that the weights (coefficients) for each variable are normally different from each other.

Optionally, the computational model on consumer segments, the computational model on healthcare provider segments, and the computational model on payor segments can also be modified based on other variables including to changes in reimbursement, changes in distribution, and consumer health dynamics. Embodiments of the present invention also include an online promotional campaign over a web browser or a mobile device that is personalized and directed to an individual consumer, rather than a consumer segment. Furthermore, embodiments of the present invention also include mechanisms for consumers to provide feedback on the brand drug using online and mobile tools and devices linked to social platforms like YouTube, Facebook, Twitter and Pinterest.

One embodiment of the overall brand value growth and retention engine 18 comprises a number of key steps as illustrated in FIG. 7 of the present invention. In this embodiment, a grocery store chain desires to launch a promotional campaign intended to increase the sales of their store chain brand of baby aspirin.

The overall brand value growth and retention engine 18 processes a combination of the following data: the computational model of consumer segment data at step 47 to identify individual segments or sub-segments of consumers who have been diagnosed or are at risk of developing heart attacks and strokes; the computation model of payor segment data at step 50 to identify individual segments or sub-segments of consumer baby aspirin users or candidates for baby aspirin by analyzing medical claims data diagnosis codes for diseases typically found in consumers who have had a prior heart attack or stroke or who are at risk of having a heart attack or stroke, in addition to other data sources in a HIPPA compliant fashion; the computation model of healthcare segment data at step 48 to identify individual segments or sub-segments HCPs who treat patients with or at risk of developing heart attacks or strokes by analyzing data on the prescribing history of individual segments or sub segments of healthcare providers using multiple sources including, but not limited to switch data, prescriber audit data and other data sources; the computational model of retail segment data at step 49 aiming to identify individual segments or sub-segments consumers who have made prior purchases of the store chain brand baby aspirin and/or other brands of baby aspirin.

The brand drug value growth and retention engine is configured to analyze customer segments and sub-segments data to identify correlations that indicate that certain combinations of customer segment data are predictive. The brand drug value growth and retention engine 18 is configure to separately analyze healthcare provider segments and sub-segments data to identify correlations that indicate that certain combinations of healthcare provider segment data are predictive. The brand drug value growth and retention engine separately analyzes retail store segments and sub-segments data to identify correlations that indicate that certain combinations of retail segment data are predictive. The brand drug value growth and retention engine 18 is configured to separately analyze payor segments and sub-segments data to identify correlations that indicate that certain combinations of payor segment data are predictive.

The brand drug value growth and retention engine 18 then is configured to combine the predictive outputs 101, 102, 145, 103 of the separate predictive computational models for consumer segment data, healthcare provider segment data, retails store segment data and payor segment data.

Simultaneously, the brand strategist 4 begins promotional planning at to assure that resources, including dollars, people and processes, are secured to support the implementation of a promotional campaign designed from the output of the predictive model.

If the predictive model at step 51 indicates the combined data are predictive, the brand strategist 4, through the computer device 3a, then deploys a promotional campaign that is comprised of consumer segment promotional plans, healthcare provider segment promotional plans, payor segment promotional plans and retailer segment promotional plans that are the product of the respective computational models for consumers, healthcare providers, payors and retailers.

In one embodiment, if the predictive model at step 51 indicates the combined data are not predictive, the output of the predictive model is used to select a different segment promotional plan modified for a specified segment within the target consumer group, a specified segment within the target HCP group, a specified segment within the target retail group and a specified segment within the target payor group for feeding back iteratively to the computational model of consumer segment data, the computational model of healthcare provider segment data and the computational model of payor segment data and the computational model of retail data for further optimization until a combination of data is deemed by the predictive model to be predictive. The computation model specifies which segments are not predictive.

In one embodiment, the brand drug value growth and retention engine 18 output might call for a promotional campaign the includes consumer segment promotional plans that include push digital advertising of the grocery store brand of baby aspirin to Facebook, Twitter, YouTube or other social media outlets. The promotional campaign might also include a retail segment promotional plan that calls for providing electronic coupons to the grocery store chain loyalty card holders distributed to the card holder's smart phones via SMS, their tablets or on their computers as an incentive for them to purchase the grocery store chain brand of baby aspirin. In the same embodiment the predictive output might call for the promotional campaign to include an HCP segment promotional plan that includes distributing paper grocery store brand baby aspirin coupons and samples to certain HCPs for redistribution to their respective patients. Given that consumers, healthcare professionals and payors have changing needs, wants, demands and behaviors, in this embodiment the application of the brand value growth and retention engine 18 continuously operates and optimizes the grocery store chain's promotional campaigns for their grocery store brand of baby aspirin until the brand strategist 4 determines that he or she no longer desires to change promotional campaign or no longer desires to continue the promotional campaign.

The predictive model determines segment promotional plans for the grocery store chain's brand of baby aspirin and determines which promotional tactic profiles require adjustment to yield a higher response rate at a certain investment level over time and therefore a promotional campaign relies on the learning machine in the predictive model to reveal which segment promotional plans are optimized or not optimized.

The brand drug value growth and retention engine 18 is configured to generate optimal segment promotional plans from the four computation models' segment data that are combined and processed through the predictive model to generate a promotional campaign based on the predictive model produced.

A promotional campaign for the grocery store chain's brand of baby aspirin comprises a plurality of segment promotional plans. Each segment promotional plan is directed to a particular segment of consumers, a particular segment of healthcare providers, a particular segment of payors and a specific segment of retailers with specific tactics to which a respective segment responds. Different segments of consumers, segments of healthcare providers, segments of retailers and segments of payors may have the same or different sets of promotional tactics that are applied in order to have the predictive model produce an effective promotional campaign.

FIG. 6B is a graphical elasticity curve illustrating different promotional tactics 69, 70, 71 and 72. The x-axis on the curve denotes promotional pressure 73 and the y-axis on the curve denotes the brand drug volume 74. Each of the promotional tactics 69, 70, 71 and 72 has an optimal point or region in considering the promotional pressure 73 relative to the brand drug volume 74, as indicated by a rectangular point 75 depicted on the promotional tactic curve 69, a rectangular point 76 depicted on the promotional tactic curve 70, a rectangular point 77 on the promotional tactic curve 71, and a rectangular point 78 on the promotional tactic curve 72.

Figure 6C:
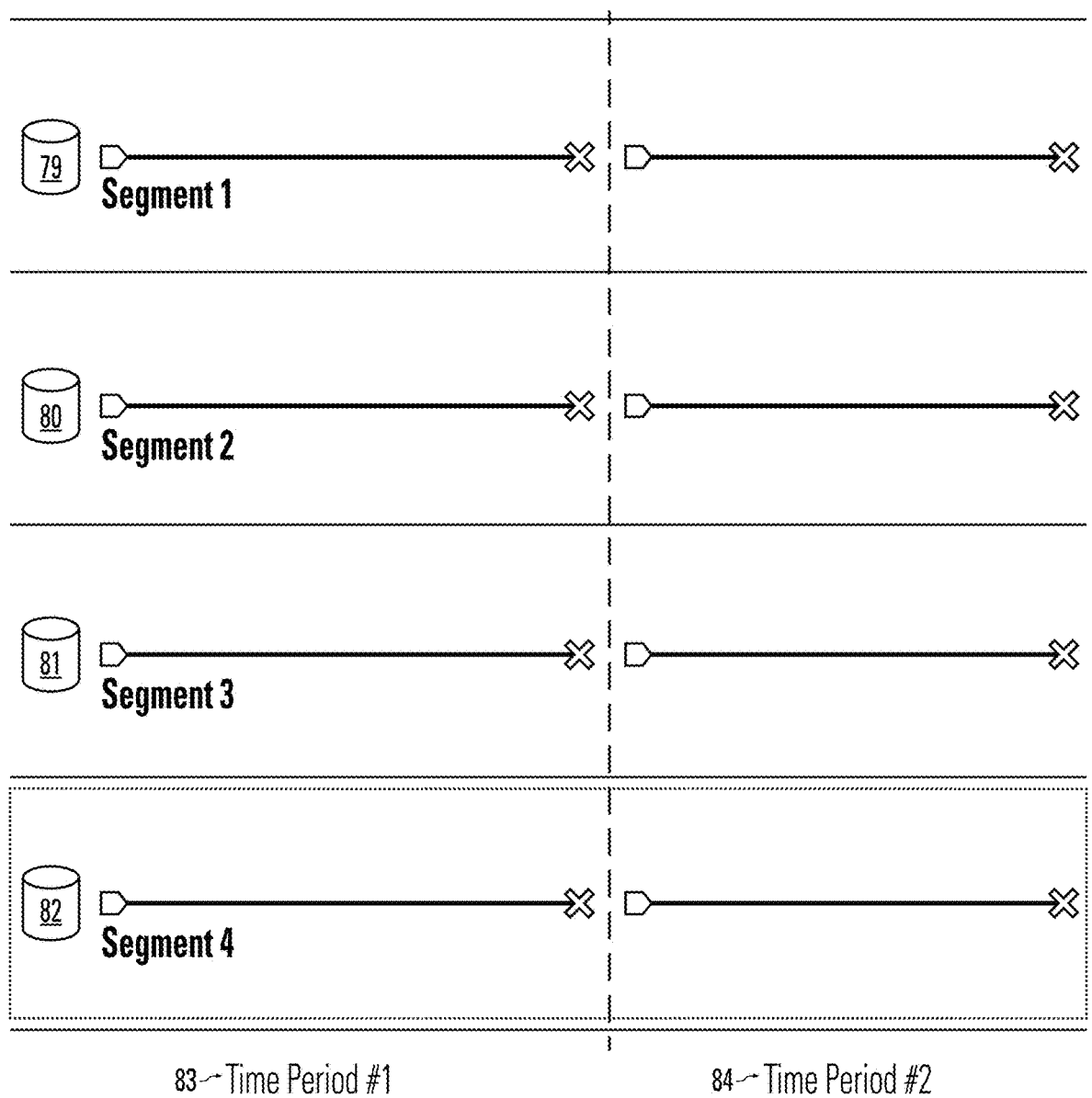
FIG. 6C is a flow diagram providing one illustration of promotional campaign at time $t_0$ with multiple promotional tactics that are applied to multiple segments of consumers.

FIG. 6C is a flow diagram providing one illustration of promotional campaign at time $t_0$ with multiple promotional tactics that are applied to multiple segments of consumers. The promotional campaign is directed to a first consumer segment 79, a second consumer segment 80, a third consumer segment 81, and a fourth consumer segment 82. Each of the first, second, third, and fourth consumer segments may involve different types of promotional tactics over time as a mechanism to adjust and achieve optimal effectiveness. At time $t_0$ as shown in FIG. 6C, four consumer segments have been identified that are associated with this promotional campaign; however, the promotional tactics have yet to be deployed during the first time period 83 and the second time period 84.

Figure 6D:
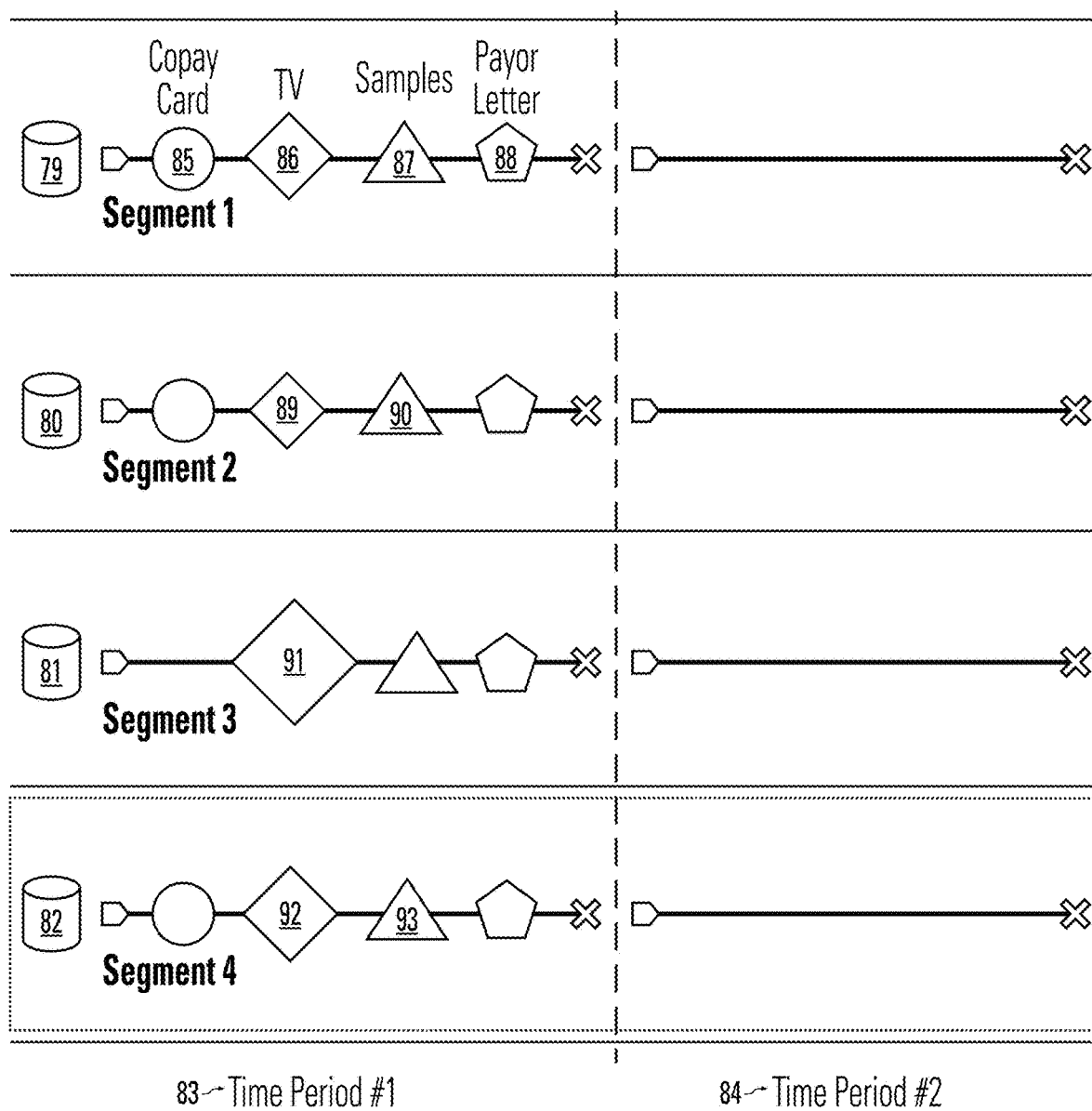
FIG. 6D is a flow diagram providing one illustration of promotional campaign during a first time period with multiple promotional tactics that are applied to multiple segments of consumers.

Various types of promotional tactics that are deployed for the four consumer segments during the first time period 83 are illustrated in FIG. 6D. In this illustration, four exemplary promotional tactics are selected, which are represented by a circular symbol for the first promotional tactic, a rectangular symbol for the second promotional tactic, a triangular symbol for the third promotional tactic, and a trapezoid symbol for the fourth promotional tactic. The symbol sizes of the circle, rectangle, triangle and trapezoid represent the amount of budget allocated for that particular promotional tactic at that point in time. For the first consumer segment 79 during the first time period 83, the promotional tactics involve the first promotional tactic 85, which in this example is a coupon/copay card for a portion during the first time period 83. The second promotional tactic 86 is then launched for a portion of time during the first time period 83 to the first consumer segment 79, which in this instance is television advertisement of the brand drug. The promotional tactic then changes to the third type of promotional tactic 87, which in this example involves providing samples of a brand drug to the first consumer segment 79 for a portion of time during the first time period 83. After the first three promotional tactics have been deployed, the fourth promotional tactic 88 supplements the previous promotional tactics by working with a payor to advertise to the first consumer segment 79. Similar types of promotional tactics and sequences are executed for the second consumer segment 80, the third consumer segment 81 and the fourth consumer segment 82 during the first time period 83. One significant difference between the promotional tactics directed to the first, second, third and fourth consumer segments is that the amount of budget allocated for a specific promotional tactic may differ depending on the suitability for that particular consumer segment. For example, the allocated budget for television advertisement 86 for the first consumer segment 79 and the television advertisement 92 for the fourth consumer segment 82 is larger than the television advertisement budget 89 for the second consumer segment 80. The amount of complementary samples 90 provided by the second consumer segment 80 is larger than the amount of samples 87 provided to the first consumer segment 79 and the amount of samples 93 provided to the fourth consumer segment 82. As for the third consumer segment 81, there is no promotional tactic deployed during the initial portion of the first time period 83, but, instead, a larger television advertisement budget 91 is allocated right after the initial period.

Figure 6E:
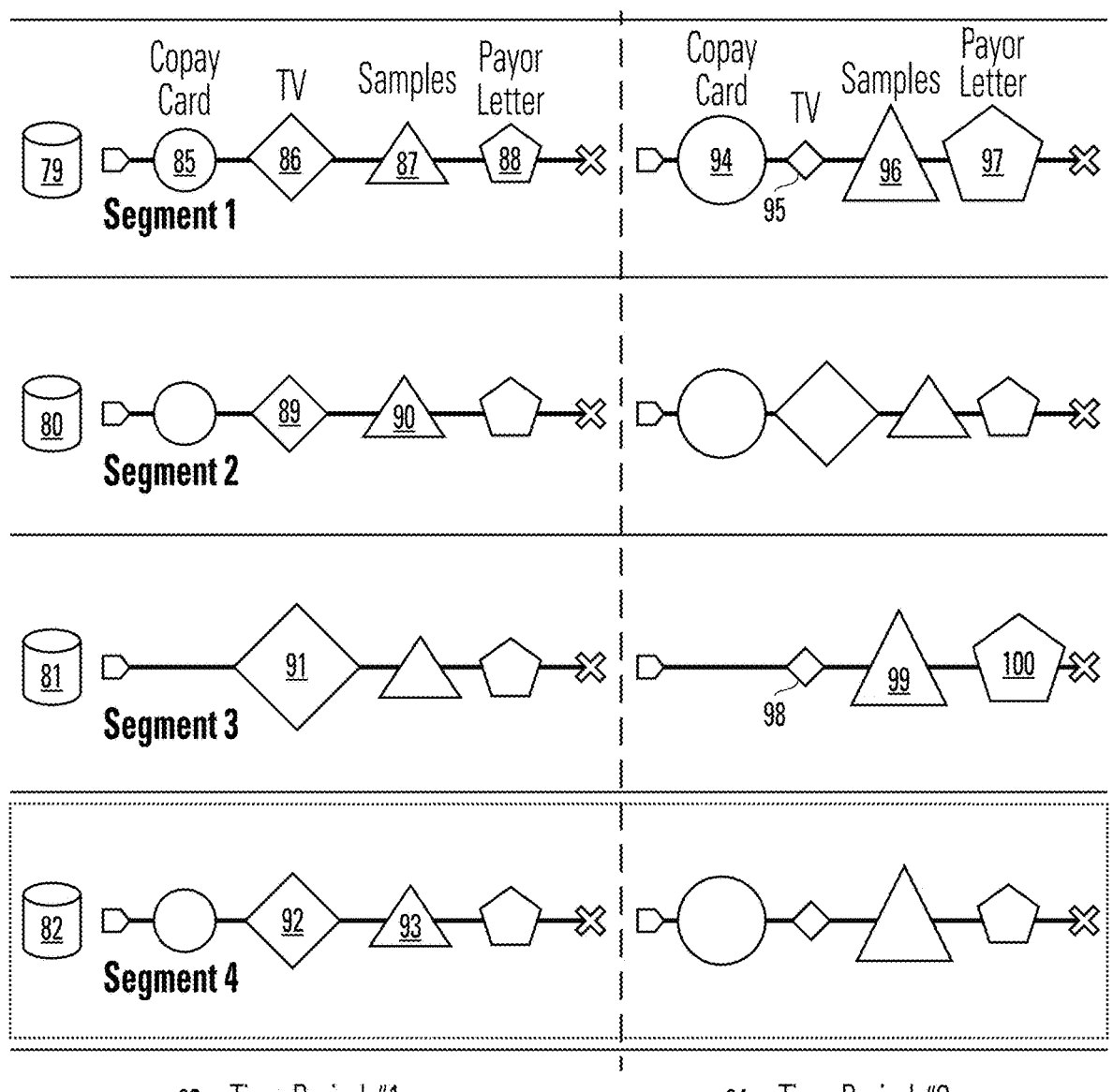
FIG. 6E is a flow diagram providing one illustration of promotional campaign during the first time period and a second time period with multiple promotional tactics that are applied to multiple segments of consumers.

Carefully selected promotional tactics deployed during the second time period 84 for the first, second, third and fourth consumer segments are illustrated in FIG. 6E. In part, based on the effectiveness of the previous promotional tactics deployed during the first time period 83, adjustments are made to the types of promotional tactics and budget sizes during the second time period 84. For example, the circle symbol representing a coupon/copay card 94 is expanded for the first consumer segment 79 during the second time period 84 relative to the first time period 83. The rectangular symbol representing television advertisement 95 is reduced for the first consumer segment 79 in the second time period 84 compared to the first time period 83. Both the triangle symbol representing samples 96 and the trapezoid symbol representing payor letter 97 are enlarged for the first consumer segment 79 in the second time period 84 in relation to the first time period 83. Significant adjustments can be made to the size of the budget allocations as shown in the third consumer segment 81; the triangle symbol representing television advertisement 98 is drastically reduced during the second time period 84 relative to the first time period 83, which may signify that the television advertisement was ineffective as a promotional tactic to the consumers in the third consumer segment 81. Instead, the amount of samples 99 and payor letter 100 are increased substantially during the second time period 84 relative to the first time period 83, perhaps an indication that the brand drug samples and advertisement through payors work quite effective during the first time period 83 for the third consumer segment 81.

Promotional tactics can vary depending on the advancement of technology as applied to segments of a population, where popular promotional tactics may include TV advertisement, Internet advertisement, social networking advertisement, direct mail advertisement, presentations by sales representatives either by telephone, computer or in person, and copay cards. Social media advertising and mobile adverting have become increasingly attractive as promotional tactics due to the large number of users. Feedbacks from these social media companies and mobile devices can serve as the basis to determine the effectiveness of a particular promotional tactic. For example, a predictive model can derive in part by "like button" on social media companies like Yelp, Facebook, and LinkedIn, or compilation of unstructured data from Twitter, Yelp, WhatsApp, Line, WeChat as well as other social media sources on consumer users' comments about brand drugs. The unstructured data from social media that have been analyzed can provide meaningful feedback into the predictive model for tracking chatters on social media or mobile devices to drug consumption behavior. Our data platform can help to uncover the online behaviors of consumers, map the promotional tactics that influence their behavior and provide insights into their engagement and buying patterns. In addition, the analysis of the unstructured data can further contribute in personalizing a promotional messaging, improving targeting and even designing new tactics to increase the effectiveness of the promotional campaigns.

Figure 8:
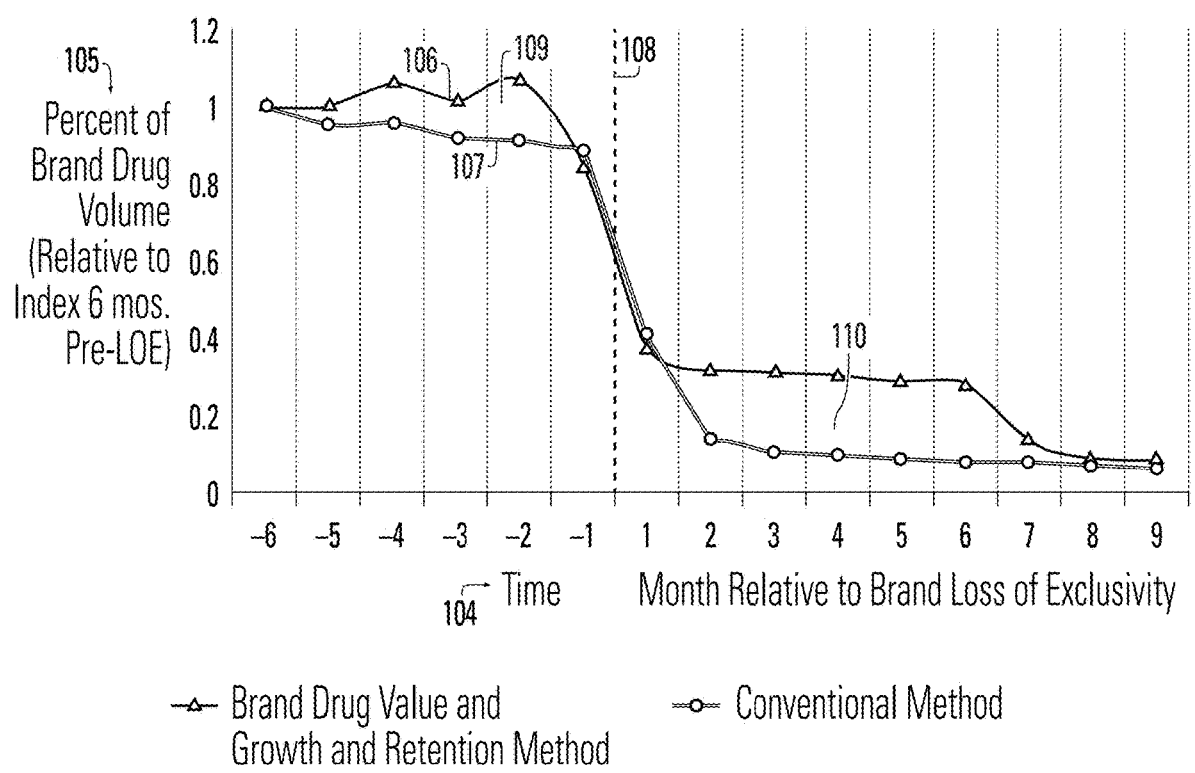
FIG. 8 is a graphical curve illustrating the impact of the incremental value to the brand drugs by the promotional campaign launched by the brand strategist relative to a conventional approach.

FIG. 8 is a graphical curve illustrating the volume of a brand drug produced by a conventional approach and compares it to the volume of the same brand drug using the promotional campaign generated by the brand value growth and retention engine 18. The curve has an x-axis 104 representing time, and a y-axis 105 denoting the percentage of brand drug volume. A dash line 108 in the center denotes when the brand drug loses exclusivity of patent. A first curve 107 represents the brand volume of the conventional approach, and a second curve 106 represents the brand volume with the impact of the promotional campaign executed by the brand drug value growth and retention engine 18. Prior to the loss of exclusivity, there in a first area 109 between the two curves 106 and 107, which shows the incremental brand drug volume produced by the promotional campaign as applied to the brand drug. After the loss of exclusivity around the time of dash line 108, there is a second area 110 between the two curves 106 and 107, which also shows the incremental value produced by the promotional campaign as applied to the brand drug. The comparison of the two exemplary curves, 106, 107, illustrates in particular that the first curve has data points without a promotional campaign, leading to loss in value both before and after LOE.

Figure 9A:
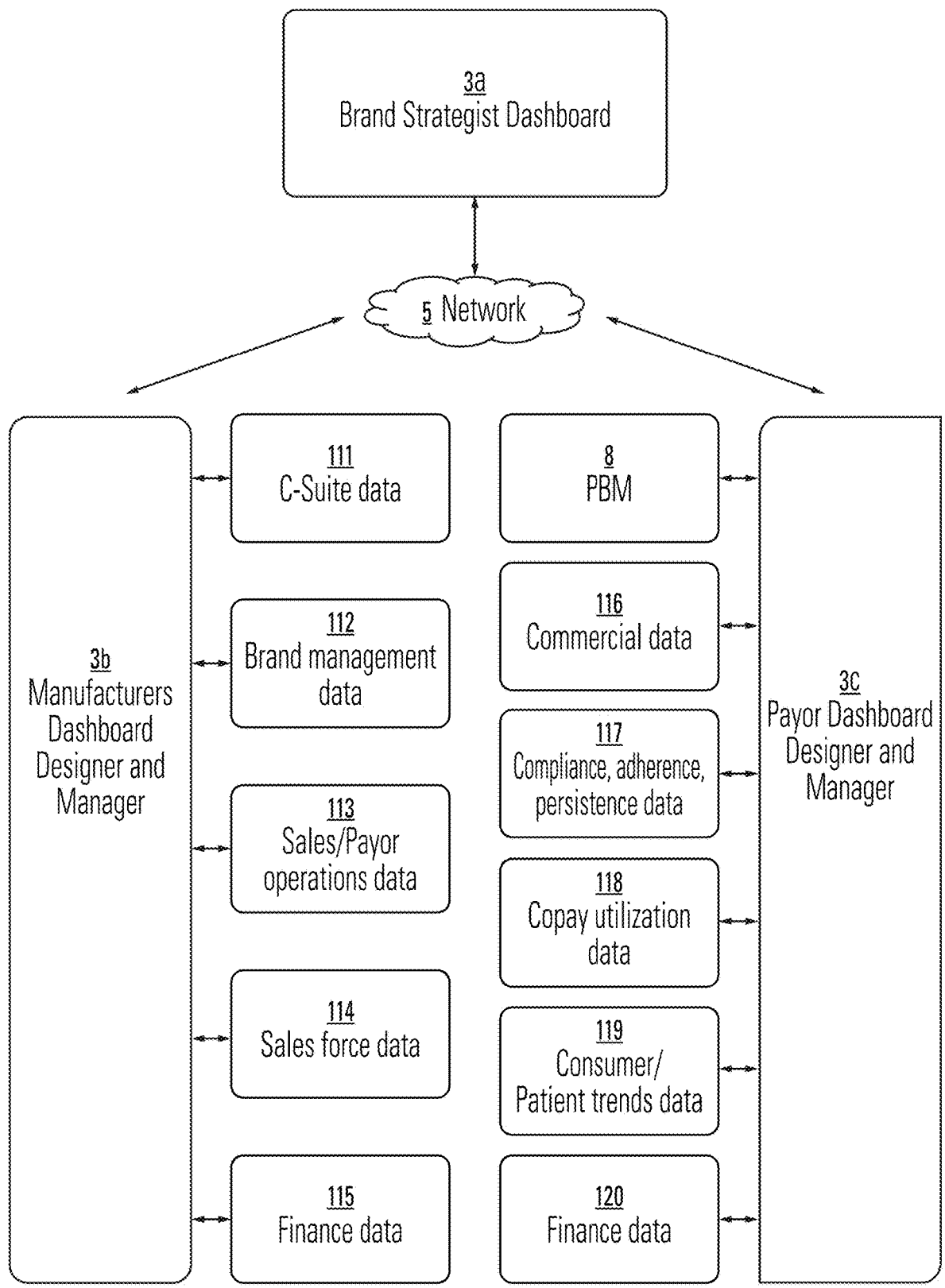
FIG. 9A is a flow diagram illustrating the communications between the brand strategist dashboard, the drug manufacture dashboard and the payor dashboard in accordance with the present invention.

FIG. 9A is a flow diagram illustrating the communications between the brand strategist dashboard 25, the drug manufacture dashboard 25 and the payor dashboard 25. The brand drug value growth and retention engine 18 is configured to supply data periodically, such as on a daily basis, to the brand strategist dashboard 25. The brand strategist dashboard 25, through the brand drug value growth and retention engine 18, pushes filtered and customized information to customize the manufacture dashboard 25 and the payor dashboard 25. The manufacture dashboard 25 furnishes information to and receives information from a C-suit manager 111, a brand management manager 112, a sales/payor operations manager 113, a sales force manager 114 and a finance manager 115. The payor dashboard 25 furnishes information to and receives information from the PBMs 8, the commercial manager 116, a compliance manager 117, a copay utilization manager 118, a patient trends manager 119 and a finance manager 120. The communications between the brand strategist dashboard 25, the drug manufacture dashboard 25 and the payor dashboard 25 ensures that checks and balances are maintained.

Figure 9B:
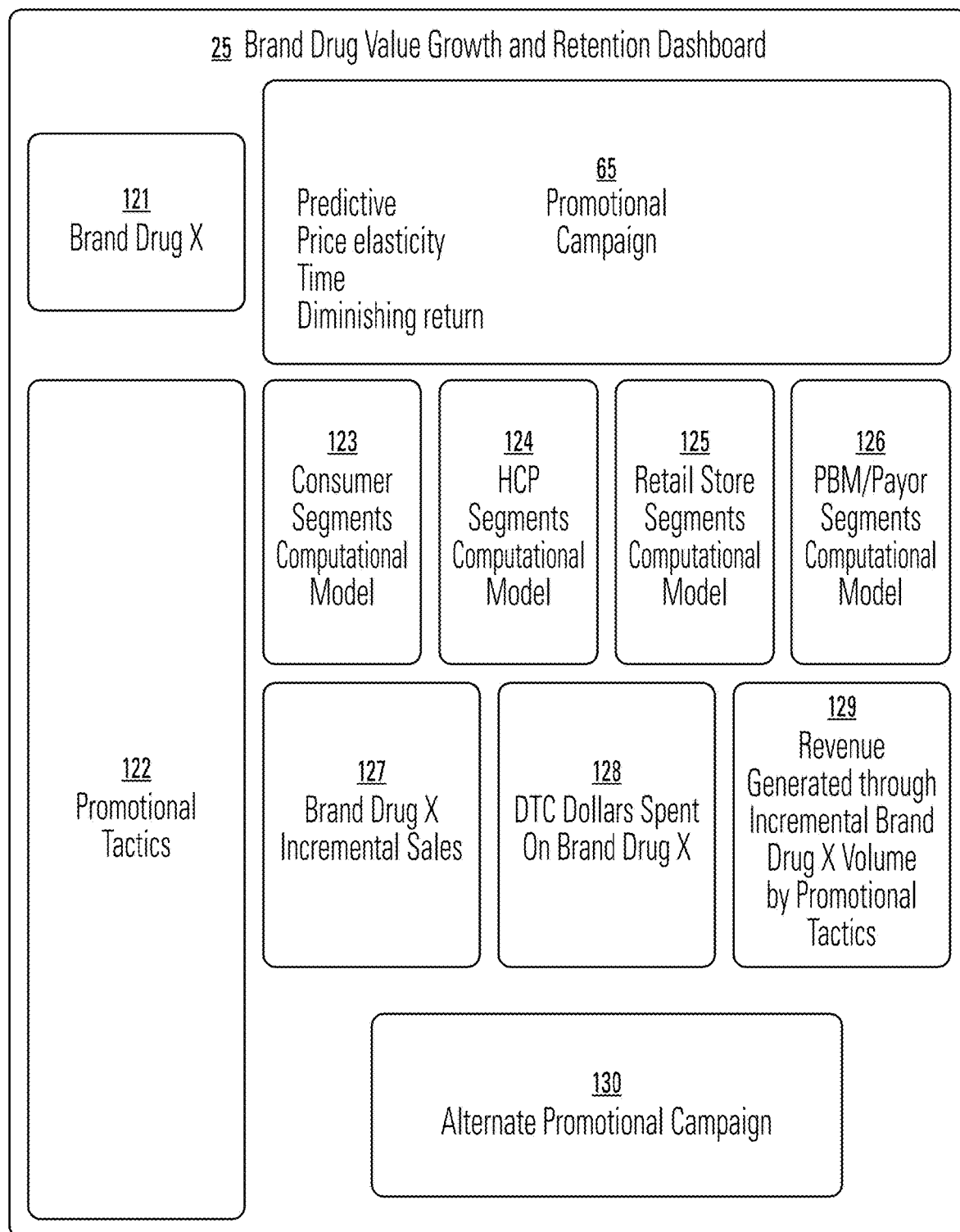
FIG. 9B is a pictorial diagram illustrating one embodiment of the brand strategist dashboard in accordance with the present invention.

FIG. 9B is a pictorial diagram illustrating one embodiment of the brand value growth and retention dashboard (also referred to as "brand strategist dashboard") 25. The brand strategist dashboard 25 displays data received from the brand drug value growth and retention engine 18 for the brand strategist 4 to manage various components of a promotional campaign. The brand strategist dashboard 25 in FIG. 9B illustrates an exemplary embodiment, and other variations and modifications of the brand strategist dashboard 25 can be implemented without departing from the spirit of the present invention. The brand strategist dashboard 25 is divided into several sections, including a brand drug section 121, a promotional campaign 65, a promotional tactics 122, a consumer segments computational model 123, a healthcare provider segments computational model 124, a retail store segments model 125, a payor segment computational model 126, a particular brand drugs X incremental sales 127, a DTC dollars spent on a particular brand drug X 128, incremental revenue generated through incremental brand drug X volume by promotional tactics 129, and an alternate promotional campaign 130. With the brand strategist dashboard 25, (clarify the dashboard) the consumer segments computational model dashboard section 123 receives data from and transmits data to step 47 which executes a computational model on consumer segments, a healthcare provider segments computational model dashboard section 124 receives data from and transmit data to step 48 which conducts a computational model on healthcare provider segments, the dashboard portion of a retail store segments model section 125 receives data from and transmit data to step 49 which executes a computational model on retail store segments, a payor segment computational model 126 receives data from and transmit data to step 50 which conducts a computational model simulation on payor segments. The financial model simulator module 26 is configured to supply the promotional campaign information to the promotional tactics 122. The consumer segments module 28a is configured to supply data to the consumer segments model section 123. The healthcare provider segments module 28b is configured to supply data to the HCP segments model section 124. The manufacturer PBM/payor strategy module 31 and the manufacturer PBM/payor execution module 32 are configured to supply to the PBM/payor computational model 126 and the retailer segments module 28c is configured to supply data to the retail store segments model section 125. The manufacturer PBM/payor strategy module 31 and the manufacturer PBM/payor execution module 32 are configured to supply to the PBM/payor computational model 126.

Figure 9C:
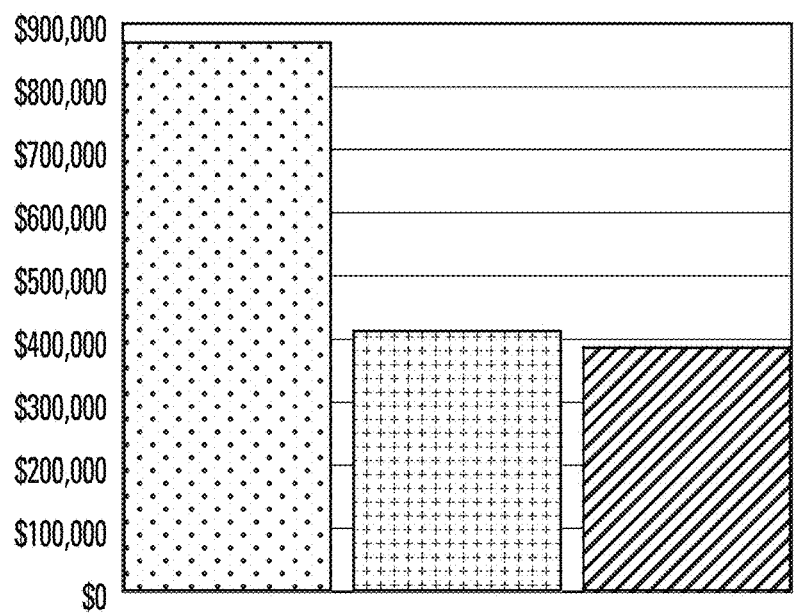
FIGS. 9C-9I are exemplary graphs that may be displayed on the brand strategist dashboard in accordance with the present invention.
Figure 9D:
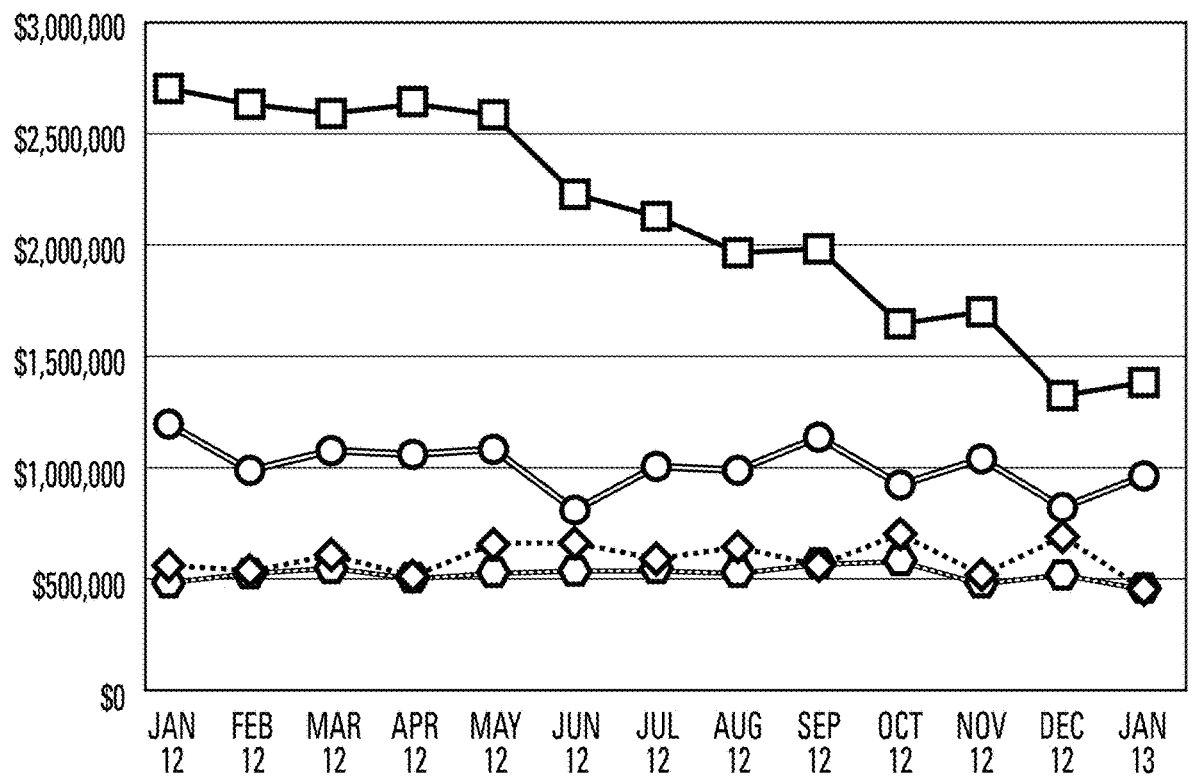
Figure 9E:
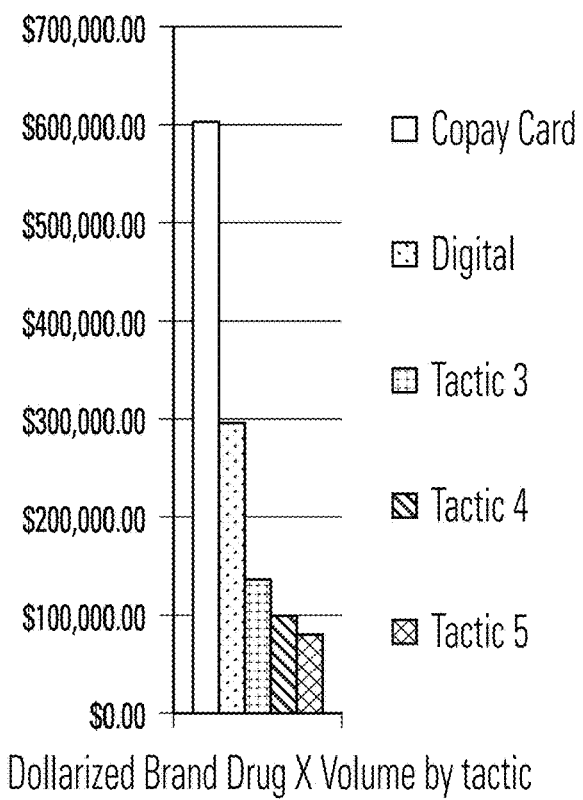
Figure 9F:
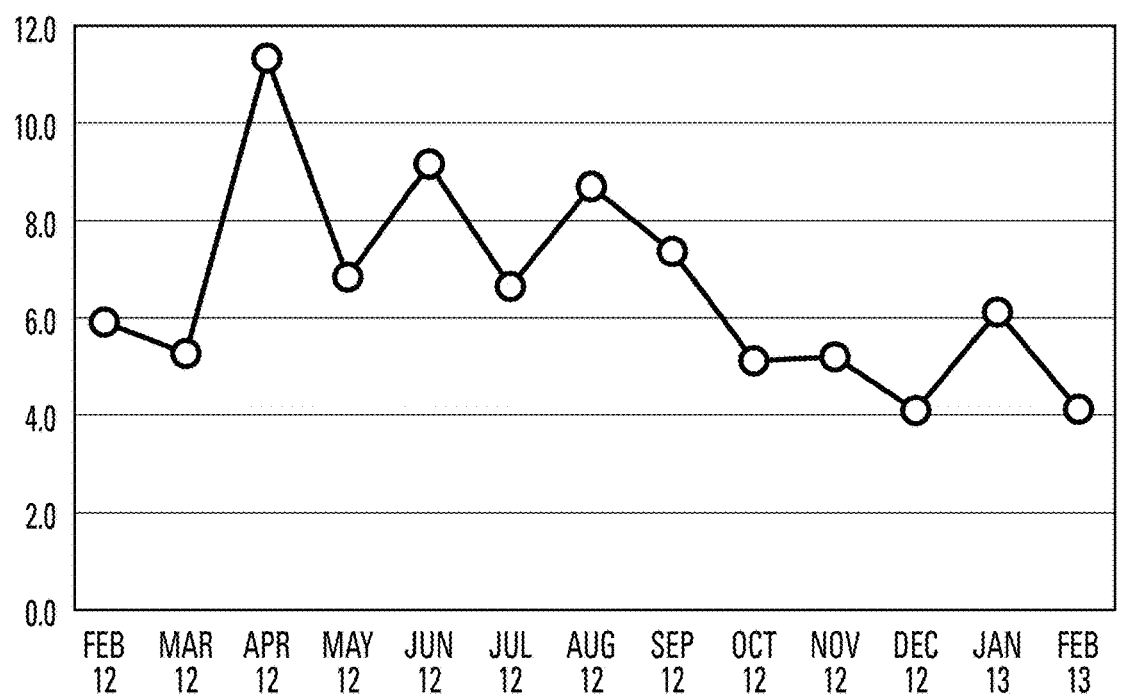
Figure 9G:
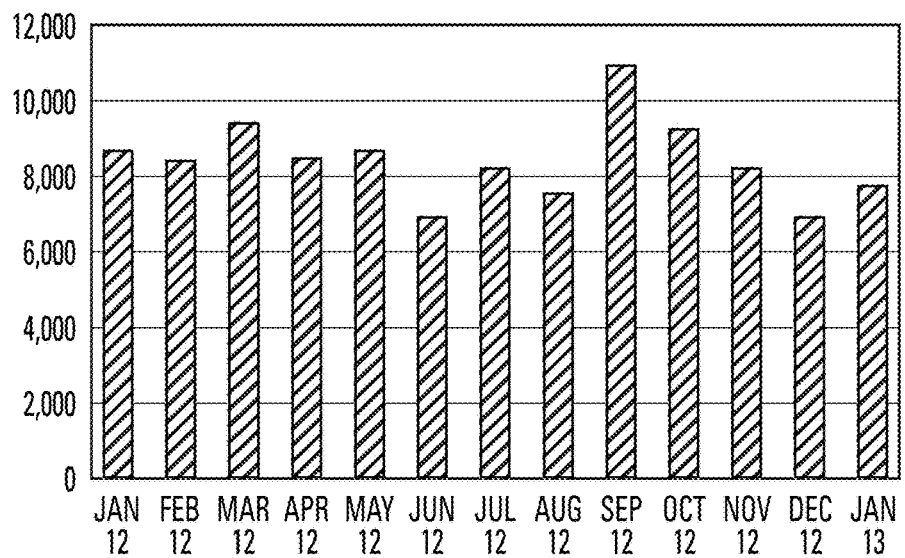
Figure 9H:
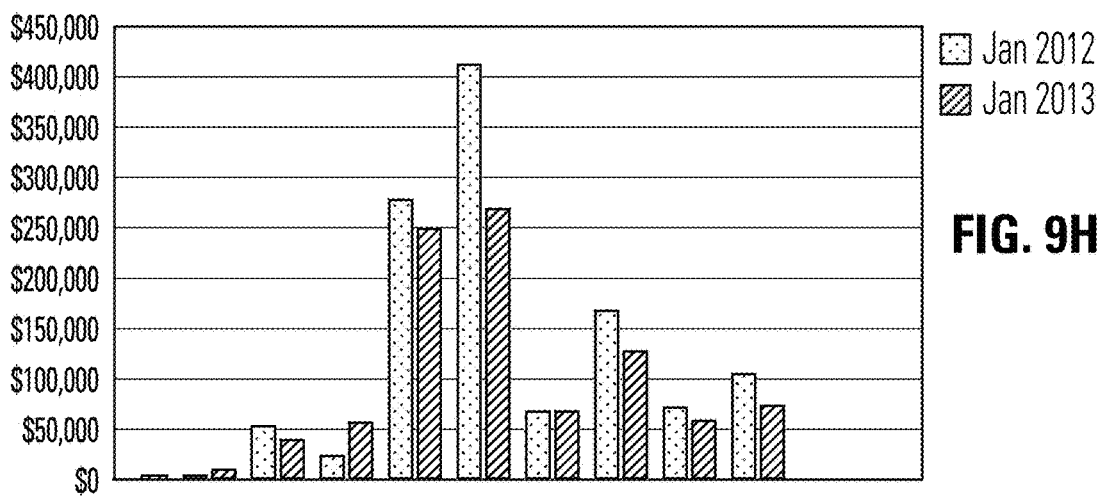
Figure 9I:
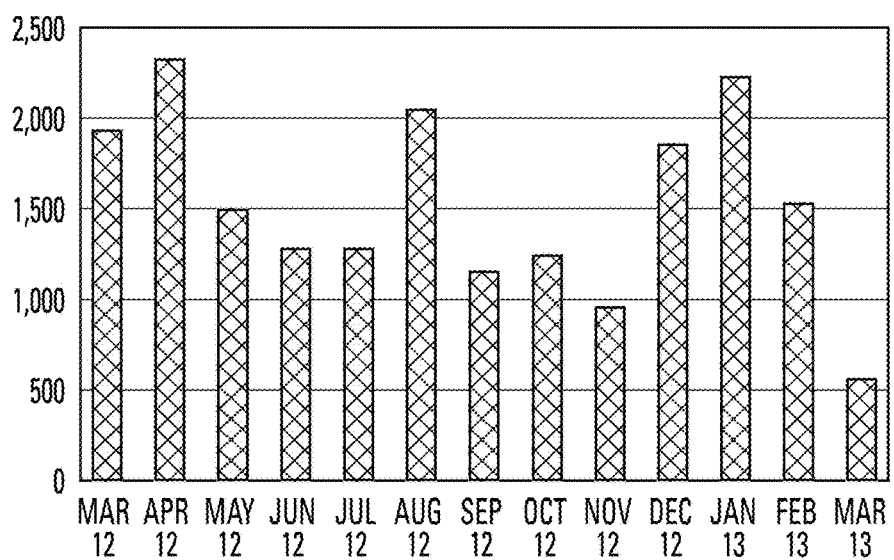

FIGS. 9C-9I are exemplary graphs that may be displayed on different sections of the brand strategist dashboard. FIG. 9C is a bar graph illustrating a particular brand drug Incremental Sales: budget, year-to-date (YTD) target, and YTD actual. FIG. 9D is a graph showing DTC dollars spent on a particular brand drug. A bar graph in FIG. 9E depicts dollars generated through incremental brand drug volume for specified months during a particular year. FIG. 9F shows PBM data for a particular brand drug copay cards redeemed by month. A sample of the copay cards distributed by a particular month for the brand drug is illustrated in FIG. 9G. FIG. 9H illustrates the amount of sales of a particular brand drug for a particular month during the current year versus the particular month from last year. A sampling of DTC exposures for a particular brand drug is depicted in FIG. 9I.

Figure 10:
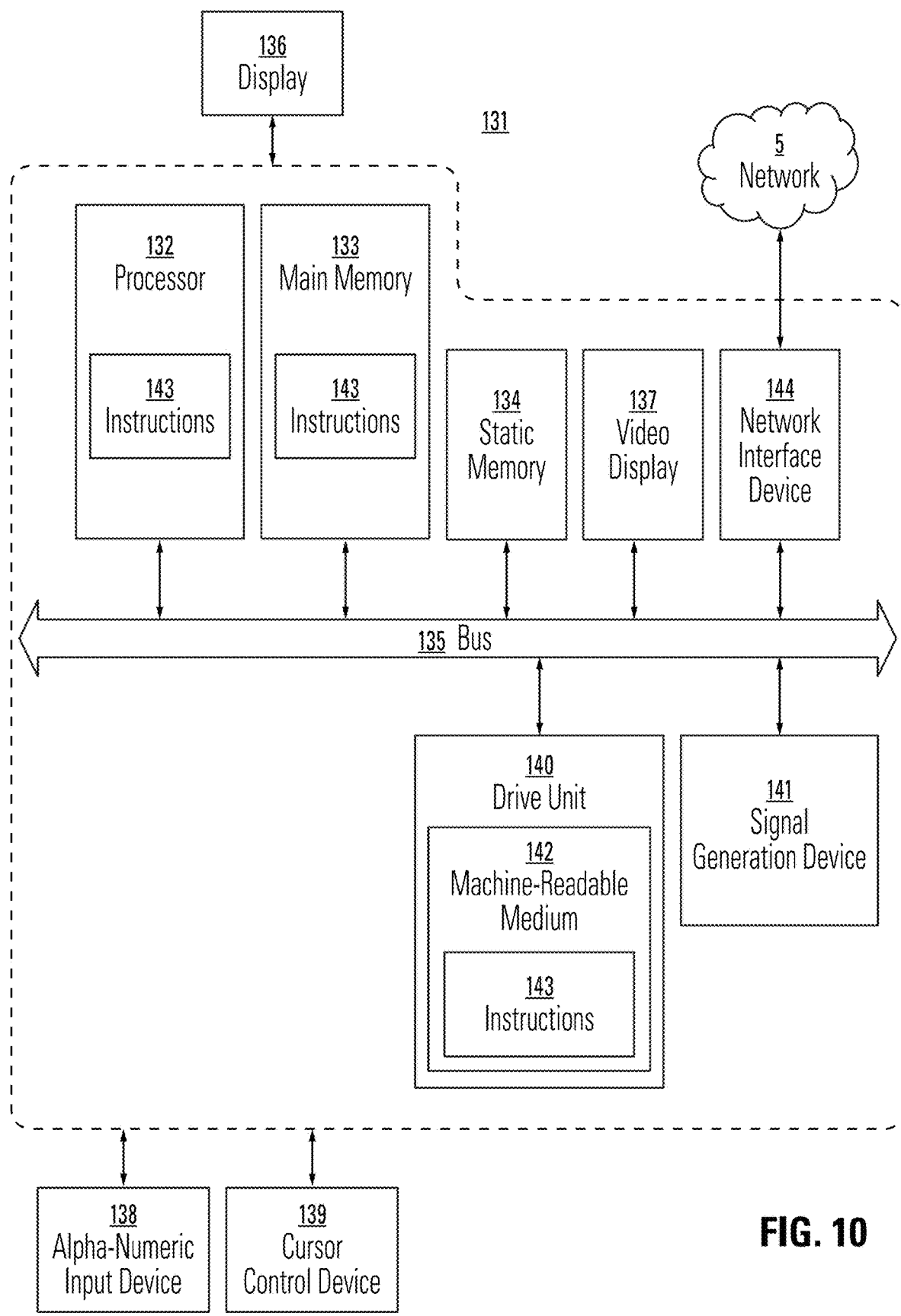
FIG. 10 is a block diagram illustrating an example of a computer device on which computer-executable instructions to perform the methodologies discussed herein may be installed and run.

FIG. 10 is a block diagram illustrating an example of a computer device, as shown in 3a, 3b, 3c, 3d, 3e, 3f, 3g, 3h, 3i and 3j, on which computer-executable instructions to perform the methodologies discussed herein may be installed and run. As alluded to above, the various computer-based devices discussed in connection with the present invention may share similar attributes. Each of the computer devices in 3a, 3b, 3c, 3d, 3e, 3f, 3g, 3h, 3i and 3j is capable of executing a set of instructions to cause the computer device to perform any one or more of the methodologies discussed herein. The computer devices may represent any or all of the 3a, 3b, 3c, 3d, 3e, 3f, 3g, 3h, 3i, and 3j server 10, or any network intermediary devices. Further, while only a single machine is illustrated, the term "machine" shall also be taken to include any collection of machines that individually or jointly execute a set (or multiple sets) of instructions to perform any one or more of the methodologies discussed herein. The exemplary computer system 131 includes a processor 132 (e.g., a central processing unit (CPU), a graphics processing unit (GPU), or both), a main memory 133 and a static memory 134, which communicate with each other via a bus 135 and project onto a display 136. The computer system 131 may further include a video display unit 137 (e.g., a liquid crystal display (LCD)). The computer system 131 also includes an alphanumeric input device 138 (e.g., a keyboard), a cursor control device 139 (e.g., a mouse), a disk drive unit 140, a signal generation device 141 (e.g., a speaker), and a network interface device 144.

The disk drive unit 140 includes a machine-readable medium 142 on which is stored one or more sets of instructions (e.g., software 143) embodying any one or more of the methodologies or functions described herein. The software 143 may also reside, completely or at least partially, within the main memory 133 and/or within the processor 132 during execution thereof, the computer system 131, the main memory 133, and the instruction-storing portions of the processor 132 also constituting machine-readable media. The software 143 may further be transmitted or received over a network 5 via the network interface device 144.

While the machine-readable medium 142 is shown in an exemplary embodiment to be a single medium, the term "machine-readable medium" should be taken to include a single medium or multiple media (e.g., a centralized or distributed database, and/or associated caches and servers) that store one or more sets of instructions. The term "machine-readable medium" shall also be taken to include any tangible medium that is capable of storing a set of instructions for execution by the machine and that cause the machine to perform any one or more of the methodologies of the present invention. The term "machine-readable medium" shall accordingly be taken to include, but not be limited to, solid-state memories, and optical and magnetic media.

The present invention has been described in particular detail with respect to possible embodiments. Those skilled in the art will appreciate that the invention may be practiced in other embodiments. The particular naming of the components, capitalization of terms, the attributes, data structures, or any other programming or structural aspect is not mandatory or significant, and the mechanisms that implement the invention or its features may have different names, formats or protocols. The system may be implemented via a combination of hardware and software, as described, or entirely in hardware elements, or entirely in software elements. The particular division of functionality between the various system components described herein is merely exemplary and not mandatory; functions performed by a single system component may instead be performed by multiple components, and functions performed by multiple components may instead be performed by a single component.

In various embodiments, the present invention can be implemented as a system or a method for performing the above-described techniques, either singly or in any combination. In another embodiment, the present invention can be implemented as a computer program product comprising a computer-readable storage medium and computer program code, encoded on the medium, for causing a processor in a computing device or other electronic device to perform the above-described techniques.

As used herein, any reference to "one embodiment" or to "an embodiment" means that a particular feature, structure or characteristic described in connection with the embodiments is included in at least one embodiment of the invention. The appearances of the phrase "in one embodiment" in various places in the specification are not necessarily all referring to the same embodiment.

Some portions of the above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is generally perceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared, transformed, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that, throughout the description, discussions utilizing terms such as "processing" or "computing" or "calculating" or "displaying" or "determining" or the like refer to the action and processes of a computer system, or similar electronic computing module and/or device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware and/or hardware, and, when embodied in software, can be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers and/or other electronic devices referred to in the specification may include a single processor or may be architectures employing multiple processor designs for increased computing capability.

The algorithms and displays presented herein are not inherently related to any particular computer, virtualized system, or other apparatus. Various general-purpose systems may also be used with programs in accordance with the teachings herein, or it may prove convenient to construct more specialized apparatus to perform the required method steps. The required structure for a variety of these systems will be apparent from the description provided herein. In addition, the present invention is not described with reference to any particular programming language. It will be appreciated that a variety of programming languages may be used to implement the teachings of the present invention as described herein, and any references above to specific languages are provided for disclosure of enablement and best mode of the present invention.

In various embodiments, the present invention can be implemented as software, hardware, and/or other elements for controlling a computer system, computing device, or other electronic device, or any combination or plurality thereof. Such an electronic device can include, for example, a processor, an input device (such as a keyboard, mouse, touchpad, trackpad, joystick, trackball, microphone, and/or any combination thereof), an output device (such as a screen, speaker, and/or the like), memory, long-term storage (such as magnetic storage, optical storage, and/or the like), and/or network connectivity, according to techniques that are well known in the art. Such an electronic device may be portable or non-portable. Examples of electronic devices that may be used for implementing the invention include mobile phones, personal digital assistants, smartphones, kiosks, desktop computers, laptop computers, tablets, wearable devices, wearable sensors, consumer electronic devices, televisions, set-top boxes or the like. An electronic device for implementing the present invention may use an operating system such as, for example, iOS available from Apple Inc. of Cupertino, Calif., Android available from Google Inc. of Mountain View, Calif., Microsoft Windows 7 available from Microsoft Corporation of Redmond, Wash., webOS available from Palm, Inc. of Sunnyvale, Calif., or any other operating system that is adapted for use on the device. In some embodiments, the electronic device for implementing the present invention includes functionality for communication over one or more networks, including for example a cellular telephone network, wireless network, and/or computer network such as the Internet.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof are intended to cover a non-exclusive inclusion. For example, a process, method, article or apparatus that comprises a list of elements is not necessarily limited to only those elements but may include other elements not expressly listed or inherent to such process, method, article or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The terms "a" or "an," as used herein, are defined as one or more than one. The term "plurality," as used herein, is defined as two or more than two. The term "another," as used herein, is defined as at least a second or more.

The term "or" is inclusive and not exclusive, unless expressly indicated otherwise or indicated otherwise by context. Therefore, "A or B" means "A, B, or both," unless expressly indicated otherwise or indicated otherwise by context. Moreover, the term "and" is both joint and several, unless expressly indicated otherwise or indicated otherwise by context. Therefore, "A and B" means "A and B, jointly or severally," unless expressly indicated otherwise or indicated otherwise by context.

An ordinary artisan should require no additional explanation in developing the methods and systems described herein but may nevertheless find some possibly helpful guidance in the preparation of these methods and systems by examining standard reference works in the relevant art.

While the invention has been described with respect to a limited number of embodiments, those skilled in the art, having benefit of the above description, will appreciate that other embodiments may be devised which do not depart from the scope of the present invention as described herein. It should be noted that the language used in the specification has been principally selected for readability and instructional purposes, and may not have been selected to delineate or circumscribe the inventive subject matter. The terms used should not be construed to limit the invention to the specific embodiments disclosed in the specification and the claims but should be construed to include all methods and systems that operate under the claims set forth herein below. Accordingly, the invention is not limited by the disclosure, but instead its scope is to be determined entirely by the following claims.

What is claimed and desired to be secured by Letters Patent of the United States is:

1. An artificial intelligence system, comprising:
   at least one engine having one or more processors;
   a memory operable to store weight value and instructions for a neutral network, wherein during operation of the system, the memory is further operable to store intermediate results computed by the at least one engine;
   one or more means, executed by the one or more processors, for generating one or more computational models on an amount of predetermined segment data retrieved via the engine from one or more electronic memories to determine a first output data, the first output data representing a predetermined threshold outcome of a drug type promotional mix from a first combination of promotional electronic methodologies;
   the one or more processors generating a predictive computational model from one or more means for a drug type to retain the drug value over time; and a machine learning means of real time data or historical data for optimizing the parameters for prediction of one or more computational models.

2. The system of claim 1, wherein the predictive computational model infers, refines or adapts the parameters of a predictive model based on past or current training data.

3. The method of claim 1, wherein the predictive computational model is adapted via the application of a learning machine that estimates parameters thereby generating a transformed predictive model.

4. The method of claim 1, wherein the predictive computational model is adapted via the application of a learning machine that modifies existing parameters thereby generating a transformed predictive model.

5. The system of claim 1, wherein the machine learning comprises one or more decision trees, one or more random forests, one or more Bayesian classifiers, one or more neural networks, one or more support vector machines, or a logistic regression.

6. The system of claim 1, wherein the one or more means comprises a first means, executed by the one or more processors, for generating a first computational model on the amount of predetermined segment data retrieved via the engine from one or more electronic memories to determine a first output data, the first output data representing a highest-valued outcome of a drug type promotional mix from a first combination of promotional electronic methodologies.

7. The system of claim 1, wherein the one or more means comprises a second means, executed by the one or more processors, for generating a second computational model on an amount of predefined healthcare provider data retrieved via the engine from the one or more electronic memories to determine a second output data, the second output data representing a highest-valued outcome of a drug type promotional mix from a second combination of promotional electronic methodologies.

8. The system of claim 1, wherein the one or more means comprises a third means, executed by the one or more processors, for generating a third computational model on an amount of predefined retail data retrieved via the engine from the one or more electronic memories to determine a third output data, the third output data representing a highest-valued outcome product mix.

9. The system of claim 1, wherein the amount of predetermined segment data comprises an amount of predefined consumer data.

10. The system of claim 1, wherein the predetermined threshold comprises a highest-valued outcome.

11. The system of claim 1, wherein the one or more electronic memories comprises one or more virtual databases.

12. The system of claim 1, wherein the one or more electronic memories comprises one or more logical databases.

13. The system of claim 1, wherein the one or more electronic memories comprises one or more distributed databases.

14. The system of claim 1, wherein the one or more electronic memories comprises a centralized database.

* * * * *